(12) United States Patent
Kim et al.

(10) Patent No.: US 10,913,715 B2
(45) Date of Patent: Feb. 9, 2021

(54) CRYSTALLINE FORM OF 1-(5-(2,4-DIFLUOROPHENYL)-1-((3-FLUOROPHENYL)SULFONYL)-4-METHOXY-1H-PYRROL-3-YL)-N-METHYLMETHANAMINE SALT

(71) Applicant: Daewoong Pharmaceutical Co., Ltd., Gyeonggi-do (KR)

(72) Inventors: Aeri Kim, Seoul (KR); Kwan Hyung Cho, Busan (KR)

(73) Assignee: Daewoong Pharmaceutical Co., Ltd., Gyeonggi-do (KR)

( * ) Notice: Subject to any disclaimer, the term of this patent is extended or adjusted under 35 U.S.C. 154(b) by 0 days.

(21) Appl. No.: 16/718,286

(22) Filed: Dec. 18, 2019

(65) Prior Publication Data

US 2020/0181082 A1 Jun. 11, 2020

Related U.S. Application Data

(62) Division of application No. 16/411,270, filed on May 14, 2019, which is a division of application No. 16/073,359, filed as application No. PCT/KR2017/002914 on Mar. 17, 2017, now Pat. No. 10,336,695.

(30) Foreign Application Priority Data

Mar. 25, 2016 (KR) .................. 10-2016-0036080

(51) Int. Cl.
C07D 207/48 (2006.01)
A61K 31/40 (2006.01)

(52) U.S. Cl.
CPC ............ C07D 207/48 (2013.01); A61K 31/40 (2013.01); *C07B 2200/13* (2013.01)

(58) Field of Classification Search
CPC .................................................. C07D 207/48
See application file for complete search history.

(56) References Cited

U.S. PATENT DOCUMENTS

| | | | |
|---|---|---|---|
| 8,048,909 B2 | 11/2011 | Kajino et al. | |
| 8,338,461 B2 | 12/2012 | Kajino et al. | |
| 9,388,133 B2 | 7/2016 | Lan et al. | |
| 10,100,010 B1 | 10/2018 | Lee et al. | |
| 10,336,695 B2 | 7/2019 | Kim et al. | |
| 10,487,053 B2 * | 11/2019 | Kim ......................... | A61P 1/04 |
| 2010/0113524 A1 | 5/2010 | Garst et al. | |
| 2011/0288040 A1 | 11/2011 | Hasuoka et al. | |
| 2015/0307449 A1 | 10/2015 | Lan et al. | |
| 2016/0200681 A1 | 7/2016 | Yu et al. | |
| 2019/0031609 A1 | 1/2019 | Kim et al. | |

FOREIGN PATENT DOCUMENTS

| | | |
|---|---|---|
| CN | 104447491 A | 3/2015 |
| EP | 1803709 A1 | 7/2007 |
| JP | 2008-522952 A | 7/2008 |
| JP | 2015-537011 A | 12/2015 |
| KR | 10-2007-0060133 | 6/2007 |
| KR | 20150027332 A | 3/2015 |
| KR | 20150084974 A | 7/2015 |
| WO | WO-2008/108380 A2 | 9/2008 |
| WO | WO-2016/175555 A2 | 11/2016 |
| WO | WO-2017/164576 A1 | 9/2017 |

OTHER PUBLICATIONS

International Search Report and Written Opinion in International Application No. PCT/KR2017/002914 dated May 30, 2017, 9 pages.
Rabon et al., Preparation of Gastric H+, K+-ATPase, Methods in Enzymology, vol. 157, Academic Press Inc. 1988, pp. 649-654.
Extended European Search Report in EP Application No. 17770546.4 dated Jul. 12, 2019, 6 pages.
Blangetti et al., "LIC-KOR-Promoted Synthesis of Alkoxydienyl Amines: An Entry to 2,3,4,5-Tetrasubstituted Pyrroles", Organic Letters, vol. 11, No. 17, 2009, pp. 3914-3917.
Notice of Allowance in JP Application No. 2018-549562 dated Jun. 25, 2019, 5 pages.
Examiner's Report in CA Application No. 3,014,745 dated Aug. 26, 2019, 3 pages.
Office Action in CO Application No. NC2018/0008833 dated Sep. 20, 2019, 8 pages.
Report of Prior Art Search for the Request for Accelerated Examination of Corresponding KR Application No. 10-2016-0036080 dated Oct. 23, 2019, 8 pages.
Office Action in CL Application No. 201802416 dated Oct. 11, 2019, 15 pages.
Office Action in KR Application No. 10-2016-0036080 dated Nov. 25, 2019, 5 pages.

* cited by examiner

*Primary Examiner* — Golam M Shameem
(74) *Attorney, Agent, or Firm* — Marshall, Gerstein & Borun LLP

(57) ABSTRACT

The present invention provides a novel crystalline form I of hydrochloride, a crystalline form II of hydrochloride, a crystalline form of succinate, a crystalline form of tartrate, a crystalline form I of fumarate and a crystalline form II of fumarate of 1-(5-(2,4-difluorophenyl)-1-((3-fluorophenyl)sulfonyl)-4-methoxy-1H-pyrrol-3-yl)-N-methylmethanamine. The above-described novel crystalline forms have high solubility in water and excellent stability under moisture-proof conditions and high-humidity exposure conditions, and thus can be pharmaceutically used.

2 Claims, 14 Drawing Sheets

CRYSTALLINE FORM OF 1-(5-(2,4-DIFLUOROPHENYL)-1-((3-FLUOROPHENYL)SULFONYL)-4-METHOXY-1H-PYRROL-3-YL)-N-METHYLMETHANAMINE SALT

CROSS-REFERENCE TO RELATED APPLICATIONS

This application is a divisional of U.S. application Ser. No. 16/411,270 filed May 14, 2019, which is a divisional of U.S. application Ser. No. 16/073,359, now U.S. Pat. No. 10,336,695 issued Jul. 2, 2019, which is the U.S. National Stage of International Application No. PCT/KR2017/002914 filed Mar. 17, 2017, which claims the priority benefit of KR Application No. 10-2016-0036080 filed Mar. 25, 2016, the entire respective disclosures of which are incorporated herein by reference.

TECHNICAL FIELD

The present invention relates to a novel crystalline form of a pharmaceutically acceptable salt of 1-(5-(2,4-difluorophenyl)-1-((3-fluorophenyl)sulfonyl)-4-methoxy-1H-pyrrol-3-yl)-N-methylmethanamine.

BACKGROUND OF ART

The selection of pharmaceutically acceptable salts and their crystalline polymorphs is a critical step in the process for researching and developing new medicines. This is because salts or crystalline polymorphs of certain medicines can often be important determinants of ease of preparation of medicine raw materials, solubility, stability during distribution and storage, ease of formulation and pharmacokinetic properties. When the same corresponding composition is crystallized in a different lattice arrangement which results in specific different thermodynamic properties and stabilities, a crystalline polymorph is produced. When two or more crystalline polymorphic substances can be produced, it is preferable to adopt a method of making a pharmaceutically excellent crystalline polymorph into a pure form.

Upon selecting the desired crystalline polymorphism, the properties of many crystalline polymorphs should be compared, and preferred crystalline polymorphisms are selected based on many types of physical properties. One crystalline polymorphic form may be desirable in some circumstances where certain aspects such as ease of manufacture, stability, etc. are deemed important, and in other situations, other crystalline polymorphs may be desirable in terms of greater solubility and/or predominantly pharmacokinetic properties.

In particular, there is a continuing need for drug formulations that exhibit better bioavailability or better stability, and thus continuous research for novel acceptable salts or purer salts of existing medicine molecules and their crystalline forms has been conducted.

Thus, the present inventors have found that a salt of 1-(5-(2,4-difluorophenyl)-1-((3-fluorophenyl)sulfonyl)-4-methoxy-1H-pyrrol-3-yl)-N-methylmethanamine, which is a new active medicinal substance, and a novel crystalline form thereof can be prepared and they can be pharmaceutically used based on their physicochemical properties and stabilities, thereby completing the present invention.

DETAILED DESCRIPTION OF THE INVENTION

Technical Problem

It is an object of the present invention to provide a novel crystalline form of a pharmaceutically acceptable salt of 1-(5-(2,4-difluorophenyl)-1-((3-fluorophenyl)sulfonyl)-4-methoxy-1H-pyrrol-3-yl)-N-methylmethanamine which has high solubility in water and excellent stability.

Technical Solution

In order to achieve the above object, the present invention provides:

a crystalline form I of 1-(5-(2,4-difluorophenyl)-1-((3-fluorophenyl)sulfonyl)-4-methoxy-1H-pyrrol-3-yl)-N-methylmethanamine hydrochloride, a crystalline form II of 1-(5-(2,4-difluorophenyl)-1-((3-fluorophenyl)sulfonyl)-4-methoxy-1H-pyrrol-3-yl)-N-methylmethanamine hydrochloride, a crystalline form of 1-(5-(2,4-difluorophenyl)-1-((3-fluorophenyl)sulfonyl)-4-methoxy-1H-pyrrol-3-yl)-N-methylmethanamine succinate, a crystalline form of 1-(5-(2,4-difluorophenyl)-1-((3-fluorophenyl)sulfonyl)-4-methoxy-1H-pyrrol-3-yl)-N-methylmethanamine tartrate, a crystalline form I of 1-(5-(2,4-difluorophenyl)-1-((3-fluorophenyl)sulfonyl)-4-methoxy-1H-pyrrol-3-yl)-N-methylmethanamine fumarate, and a crystalline form II of 1-(5-(2,4-difluorophenyl)-1-((3-fluorophenyl)sulfonyl)-4-methoxy-1H-pyrrol-3-yl)-N-methylmethanamine fumarate.

Hereinafter, the present invention will be described in detail.

A 1-(5-(2,4-difluorophenyl)-1-((3-fluorophenyl)sulfonyl)-4-methoxy-1H-pyrrol-3-yl)-N-methylmethanamine, which is a new active medicinal substance, is a compound represented by the following chemical formula (1), which corresponds to a 4-methoxypyrrole derivative:

[Chemical Formula 1]

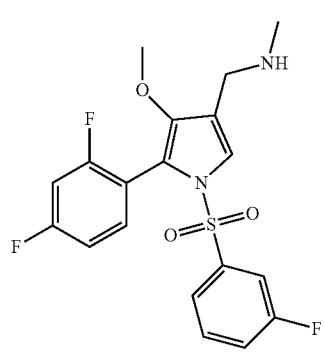

The above 1-(5-(2,4-difluorophenyl)-1-((3-fluorophenyl)sulfonyl)-4-methoxy-1H-pyrrol-3-yl)-N-methylmethanamine and a pharmaceutically acceptable salt thereof can have not only a proton pump inhibitory activity, a gastric damage inhibitory activity and a defensive-factor enhancing effect, but also excellent eradication activity against *Helicobacter pylori* (*H. pylori*). Therefore, the 1-(5-(2,4-difluorophenyl)-1-((3-fluorophenyl)sulfonyl)-4-methoxy-1H-pyrrol-3-yl)-N-methylmethanamine and a pharmaceutically acceptable salt thereof can be effectively used for the prevention and treatment of gastrointestinal injury due to gastrointestinal ulcer, gastritis, reflux esophagitis, or *H. pylori*.

The crystalline form of a pharmaceutically acceptable salt of the 1-(5-(2,4-difluorophenyl)-1-((3-fluorophenyl)sulfonyl)-4-methoxy-1H-pyrrol-3-yl)-N-methylmethanamine can be prepared by various crystallization methods such as an evaporative crystallization method, a drowning-out crystallization method, a reactive crystallization method, a solvent-mediated polymorphic transition method, and a solid-state polymorphic transition method, which are selected according to the thermodynamic and dynamic characteristics of the salt.

In addition, the crystalline form of a pharmaceutically acceptable salt of 1-(5-(2,4-difluorophenyl)-1-((3-fluorophenyl)sulfonyl)-4-methoxy-1H-pyrrol-3-yl)-N-methylmethanamine thus prepared can be identified through an X-ray powder diffraction analysis and a differential scanning calorimetry analysis.

Specifically, the above crystalline form can be classified through a diffraction angle (2θ) exhibiting a characteristic peak in an X-ray powder diffraction pattern, and an intensity of a peak according to the respective diffraction angles (2θ). Here, the diffraction angle (2θ) can be varied by ±0.2° or preferably ±0.1° due to various factors such as a manufacturing technique of the measurement sample, a fixing procedure of the measurement sample, and a measuring instrument.

In addition, the crystalline form can be distinguished through the endothermic initiation temperature and the endothermic temperature indicating the maximum endothermic peak in the differential scanning calorimetry analysis. Here, the temperature may be varied by ±3° C., preferably ±2° C., or more preferably ±1° C. depending on various factors such as a manufacturing technique of the measurement sample, a measuring instrument, and a rate of temperature change.

Crystalline Form I of 1-(5-(2,4-difluorophenyl)-1-((3-fluorophenyl)sulfonyl)-4-methoxy-1H-pyrrol-3-yl)-N-methylmethanamine hydrochloride The crystalline form I of 1-(5-(2,4-difluorophenyl)-1-((3-fluorophenyl)sulfonyl)-4-methoxy-1H-pyrrol-3-yl)-N-methylmethanamine hydrochloride may have peaks at diffraction angles (2θ±0.2°) of 5.8°, 9.7°, 10.0°, 12.8°, 13.2°, 17.4° and 18.5° in an X-ray powder diffraction pattern.

Specifically, the crystalline form I of 1-(5-(2,4-difluorophenyl)-1-((3-fluorophenyl)sulfonyl)-4-methoxy-1H-pyrrol-3-yl)-N-methylmethanamine hydrochloride may have peaks at diffraction angles (2θ±0.2°) of 5.8°, 9.7°, 10.0°, 12.8°, 13.2°, 17.4°, 18.5°, 19.5°, 19.8°, 20.1°, 25.9° and 28.2° in an X-ray powder diffraction pattern.

More specifically, the crystalline form I of 1-(5-(2,4-difluorophenyl)-1-((3-fluorophenyl)sulfonyl)-4-methoxy-1H-pyrrol-3-yl)-N-methylmethanamine hydrochloride may have peaks at diffraction angles (2θ±0.2°) of 5.8°, 9.7°, 10.0°, 12.8°, 13.2°, 17.4°, 18.5°, 19.5°, 19.8°, 20.1°, 21.8°, 25.9°, 26.5° and 28.2° in an X-ray powder diffraction pattern.

Further, the crystalline form I of 1-(5-(2,4-difluorophenyl)-1-((3-fluorophenyl)sulfonyl)-4-methoxy-1H-pyrrol-3-yl)-N-methylmethanamine hydrochloride can have an endothermic initiation temperature of 215.02±3° C. and exhibit a maximum endothermic peak at an endothermic temperature of 217.11±3° C. in a differential scanning calorimetry analysis.

The crystalline form I of 1-(5-(2,4-difluorophenyl)-1-((3-fluorophenyl)sulfonyl)-4-methoxy-1H-pyrrol-3-yl)-N-methylmethanamine hydrochloride can be prepared by an evaporative crystallization method comprising the steps of:

1) dissolving 1-(5-(2,4-difluorophenyl)-1-((3-fluorophenyl)sulfonyl)-4-methoxy-1H-pyrrol-3-yl)-N-methylmethanamine hydrochloride in one or more solvents selected from the group consisting of $C_{1-8}$ aliphatic alcohol, pentane, hexane, heptane, cyclohexane, benzene, toluene, methyl acetate, ethyl acetate, methylene chloride, chloroform, ether, petroleum ether, ethylene glycol, propylene glycol, butylene glycol, acetonitrile and acetone to prepare a solution; and 2) evaporating the solvent from the solution to crystallize the hydrochloride.

The step 1) is a step of dissolving the hydrochloride using a good solvent capable of completely dissolving the hydrochloride, and may be performed at room temperature.

Alternatively, in the step 1), a 1-(5-(2,4-difluorophenyl)-1-((3-fluorophenyl)sulfonyl)-4-methoxy-1H-pyrrol-3-yl)-N-methylmethanamine free base and a hydrochloric acid may be used instead of hydrochloride.

In this case, as the $C_{1-8}$ aliphatic alcohol, methanol, ethanol, propanol, isopropanol, n-butanol, or n-octanol may be used.

For example, the solvent may be methanol, ethanol, ethyl acetate, methylene chloride or acetone, and it can be used as a volume (ml/g) of 1-20 times, or preferably as a volume (ml/g) of 5-20 times, relative to the weight of the hydrochloride.

The step 2) is a step of evaporating the solvent from the solution prepared in the step 1) and making the solution in a supersaturated state to crystallize the hydrochloride, and may be performed at a temperature of 23° C. to 28° C. for 1 day to 4 days.

Alternatively, the crystalline form I of 1-(5-(2,4-difluorophenyl)-1-((3-fluorophenyl)sulfonyl)-4-methoxy-1H-pyrrol-3-yl)-N-methylmethanamine hydrochloride can be prepared by a drowning-out crystallization method comprising the steps of:

1) dissolving 1-(5-(2,4-difluorophenyl)-1-((3-fluorophenyl)sulfonyl)-4-methoxy-1H-pyrrol-3-yl)-N-methylmethanamine hydrochloride in one or more solvents selected from the group consisting of $C_{1-8}$ aliphatic alcohol, pentane, hexane, heptane, cyclohexane, benzene, toluene, methyl acetate, ethyl acetate, methylene chloride, chloroform, ether, petroleum ether, ethylene glycol, propylene glycol, butylene glycol, acetonitrile and acetone to prepare a solution; and 2) adding and stirring one or more crystallization solvents selected from the group consisting of $C_{1-8}$ aliphatic alcohol, water and an organic solvent to the solution to crystallize the hydrochloride.

The step 1) can be carried out in the same manner as in step 1 of the above-described evaporative crystallization method.

The step 2) is a step of adding an anti-solvent to the solution prepared in the step 1) to change the solubility, thereby crystallizing a hydrochloride, wherein the stirring can be carried out at a speed of 50 rpm to 300 rpm at a temperature 23° C. to 28° C. for 1 hour to 1 day.

In this case, as the $C_{1-8}$ aliphatic alcohol, methanol, ethanol, propanol, isopropanol, n-butanol or n-octanol may be used. As the organic solvent, n-hexane, ethyl acetate, butyl acetate, acetonitrile, chloroform, diethyl ether, or acetone may be used.

In addition, the crystallization solvent may be used as a volume (ml/g) of 1-20 times, or preferably as a volume (ml/g) of 5-20 times, relative to the weight of the hydrochloride, and a volume ratio of the crystallization solvent of the step 2 and the solvent of the step 1 may be 1:1 to 1:2. Within the above range, a crystal can be produced with high yield and high purity without economic loss due to an increase in the crystal generation time and an excessive use of the solvent.

The crystal produced by the evaporative crystallization method or the drowning-out crystallization method can be recovered from the solution by a vacuum filtration process. If necessary, the recovered crystal may be washed and dried under vacuum to obtain a crystalline form of hydrochloride having a high purity. In addition, the reaction conditions such as the ratio of solvent, the temperature range, the process time, and the like described in the above preparation methods can be adjusted depending on the selected solvent.

Crystalline Form II of 1-(5-(2,4-difluorophenyl)-1-((3-fluorophenyl)sulfonyl)-4-methoxy-1H-pyrrol-3-yl)-N-methylmethanamine hydrochloride The crystalline form II of 1-(5-(2,4-difluorophenyl)-1-((3-fluorophenyl)sulfonyl)-4-methoxy-1H-pyrrol-3-yl)-N-methylmethanamine hydrochloride may have peaks at diffraction angles (2θ±0.2°) of 9.2°, 10.0°, 12.9° and 20.2° in an X-ray powder diffraction pattern.

Specifically, the crystalline form II of 1-(5-(2,4-difluorophenyl)-1-((3-fluorophenyl)sulfonyl)-4-methoxy-1H-pyrrol-3-yl)-N-methylmethanamine hydrochloride may have peaks at diffraction angles (2θ±0.2°) of 9.2°, 9.8°, 10.0°, 12.9°, 13.2°, 13.4°, 13.8°, 15.0°, 18.4°, 19.6° and 20.2° in an X-ray powder diffraction pattern.

Further, the crystalline form II of 1-(5-(2,4-difluorophenyl)-1-((3-fluorophenyl)sulfonyl)-4-methoxy-1H-pyrrol-3-yl)-N-methylmethanamine hydrochloride can have an endothermic initiation temperature of 213.14±3° C. and exhibit a maximum endothermic peak at an endothermic temperature of 215.7±3° C. in a differential scanning calorimetry analysis.

The crystalline form II of 1-(5-(2,4-difluorophenyl)-1-((3-fluorophenyl)sulfonyl)-4-methoxy-1H-pyrrol-3-yl)-N-methylmethanamine hydrochloride can be prepared by an evaporative crystallization method by which the solvent of the step 1) is used as a volume (ml/g) of 5-50 times, or preferably as a volume (ml/g) of 30-50 times, relative to the weight of the hydrochloride.

Crystalline Form of 1-(5-(2,4-difluorophenyl)-1-((3-fluorophenyl)sulfonyl)-4-methoxy-1H-pyrrol-3-yl)-N-methylmethanamine succinate The crystalline form of 1-(5-(2,4-difluorophenyl)-1-((3-fluorophenyl)sulfonyl)-4-methoxy-1H-pyrrol-3-yl)-N-methylmethanamine succinate may have peaks at diffraction angles (2θ±0.2°) of 8.0°, 11.2°, 12.0°, 14.9°, 22.1° and 24.1 in an X-ray powder diffraction pattern.

Specifically, the crystalline form of 1-(5-(2,4-difluorophenyl)-1-((3-fluorophenyl)sulfonyl)-4-methoxy-1H-pyrrol-3-yl)-N-methylmethanamine succinate may have peaks at diffraction angles (2θ±0.2°) of 8.0°, 11.2°, 12.0°, 14.9°, 20.0°, 22.1° and 24.1° in an X-ray powder diffraction pattern.

Further, the crystalline form of 1-(5-(2,4-difluorophenyl)-1-((3-fluorophenyl)sulfonyl)-4-methoxy-1H-pyrrol-3-yl)-N-methylmethanamine succinate can have an endothermic initiation temperature of 132.3±3° C. and exhibit a maximum endothermic peak at an endothermic temperature of 133.9±3° C. in a differential scanning calorimetry analysis.

The crystalline form of 1-(5-(2,4-difluorophenyl)-1-((3-fluorophenyl)sulfonyl)-4-methoxy-1H-pyrrol-3-yl)-N-methylmethanamine succinate can be prepared by using the evaporative crystallization method or the drowning-out crystallization method similarly to the crystalline form I of hydrochloride, except that succinate was used instead of hydrochloride.

Crystalline Form of 1-(5-(2,4-difluorophenyl)-1-((3-fluorophenyl)sulfonyl)-4-methoxy-1H-pyrrol-3-yl)-N-methylmethanamine tartrate The crystalline form of 1-(5-(2,4-difluorophenyl)-1-((3-fluorophenyl)sulfonyl)-4-methoxy-1H-pyrrol-3-yl)-N-methylmethanamine tartrate may have peaks at diffraction angles (2θ±0.2°) of 11.7°, 21.5° and 23.5° in an X-ray powder diffraction pattern.

Specifically, the crystalline form of 1-(5-(2,4-difluorophenyl)-1-((3-fluorophenyl)sulfonyl)-4-methoxy-1H-pyrrol-3-yl)-N-methylmethanamine tartrate may have peaks at diffraction angles (2θ±0.2°) of 11.7°, 13.0°, 13.5°, 14.5°, 18.3°, 19.5°, 20.3°, 21.5° and 23.5° in an X-ray powder diffraction pattern.

Further, the crystalline form of 1-(5-(2,4-difluorophenyl)-1-((3-fluorophenyl)sulfonyl)-4-methoxy-1H-pyrrol-3-yl)-N-methylmethanamine tartrate can have an endothermic initiation temperature of 146.34±3° C. and exhibit a maximum endothermic peak at an endothermic temperature of 148.27±3° C. in a differential scanning calorimetry analysis.

The crystalline form of 1-(5-(2,4-difluorophenyl)-1-((3-fluorophenyl)sulfonyl)-4-methoxy-1H-pyrrol-3-yl)-N-methylmethanamine tartrate can be prepared by using the evaporative crystallization method or the drowning-out crystallization method similarly to the crystalline form I of hydrochloride, except that tartrate was used instead of hydrochloride.

Crystalline Form I of 1-(5-(2,4-difluorophenyl)-1-((3-fluorophenyl)sulfonyl)-4-methoxy-1H-pyrrol-3-yl)-N-methylmethanamine fumarate The crystalline form I of 1-(5-(2,4-difluorophenyl)-1-((3-fluorophenyl)sulfonyl)-4-methoxy-1H-pyrrol-3-yl)-N-methylmethanamine fumarate may have peaks at diffraction angles (2θ0.2°) of 7.9°, 11.9° and 24.0 in an X-ray powder diffraction pattern.

Specifically, the crystalline form I of 1-(5-(2,4-difluorophenyl)-1-((3-fluorophenyl)sulfonyl)-4-methoxy-1H-pyrrol-3-yl)-N-methylmethanamine fumarate may have peaks at diffraction angles (2θ0.2°) of 7.9°, 11.9°, 20.0 and 24.0° in an X-ray powder diffraction pattern.

Further, the crystalline form I of 1-(5-(2,4-difluorophenyl)-1-((3-fluorophenyl)sulfonyl)-4-methoxy-1H-pyrrol-3-yl)-N-methylmethanamine fumarate can have an endothermic initiation temperature of 164.97±3° C. and exhibit a maximum endothermic peak at an endothermic temperature of 167.46±3° C. in a differential scanning calorimetry analysis.

The crystalline form I of 1-(5-(2,4-difluorophenyl)-1-((3-fluorophenyl)sulfonyl)-4-methoxy-1H-pyrrol-3-yl)-N-methylmethanamine fumarate can be prepared by using the evaporative crystallization method similarly to the crystalline form I of hydrochloride, except that fumarate was used instead of hydrochloride.

Alternatively, the crystalline form I of 1-(5-(2,4-difluorophenyl)-1-((3-fluorophenyl)sulfonyl)-4-methoxy-1H-pyrrol-3-yl)-N-methylmethanamine fumarate can be prepared by a reactive crystallization method comprising the steps of:

1) dissolving a 1-(5-(2,4-difluorophenyl)-1-((3-fluorophenyl)sulfonyl)-4-methoxy-1H-pyrrol-3-yl)-N-methylmethanamine free base and a fumaric acid, respectively, in $C_{1-8}$ aliphatic alcohol to prepare a solution of 1-(5-(2,4-difluorophenyl)-1-((3-fluorophenyl)sulfonyl)-4-methoxy-1H-pyrrol-3-yl)-N-methylmethanamine free base and a fumaric acid solution; and 2) mixing the solution of 1-(5-(2,4-difluorophenyl)-1-((3-fluorophenyl)sulfonyl)-4-methoxy-1H-pyrrol-3-yl)-N-methylmethanamine free base and the fumaric acid solution and then stirring the mixed solutions to crystallize the fumarate.

The step 1) is a step of preparing a solution using a good solvent capable of completely dissolving the free base and the fumaric acid, and may be performed at room temperature.

In this case, methanol, ethanol, propanol, isopropanol, n-butanol, or n-octanol may be used as the $C_{1-8}$ aliphatic alcohol. Preferably, ethanol may be used as the $C_{1-8}$ aliphatic alcohol.

The $C_{1-8}$ aliphatic alcohol may be used as a volume (ml/g) of 5-20 times, relative to the weight of the 1-(5-(2,4-difluorophenyl)-1-((3-fluorophenyl)sulfonyl)-4-methoxy-1H-pyrrol-3-yl)-N-methylmethanamine free base, and it may be used as a volume (ml/g) of 5-30 times, relative to the weight of the fumaric acid.

The step 2) is a step of mixing the solutions prepared in the step 1) and stirring the mixture to produce a crystal by chemical reaction, wherein the stirring is carried out at a temperature of 24° C. to 28° C. at a speed of 50 to 300 rpm for 2 to 4 hours. Within this range, the crystal can be effectively produced while fumarate is formed.

The crystal produced by the reactive crystallization method can be recovered from the solution by a vacuum filtration process. If necessary, the recovered crystal may be washed and dried under vacuum to obtain a crystalline form having a high purity. In addition, the reaction conditions such as the ratio of solvent, the temperature range and the process time described in the above preparation methods can be adjusted depending on the selected solvent.

Crystalline Form II of 1-(5-(2,4-difluorophenyl)-1-((3-fluorophenyl)sulfonyl)-4-methoxy-1H-pyrrol-3-yl)-N-methylmethanamine fumarate The crystalline form II of 1-(5-(2,4-difluorophenyl)-1-((3-fluorophenyl)sulfonyl)-4-methoxy-1H-pyrrol-3-yl)-N-methylmethanamine fumarate may have peaks at diffraction angles (2θ±0.2°) of 8.4°, 10.5°, 18.3° and 19.02° in an X-ray powder diffraction pattern.

Specifically, the crystalline form II of 1-(5-(2,4-difluorophenyl)-1-((3-fluorophenyl)sulfonyl)-4-methoxy-1H-pyrrol-3-yl)-N-methylmethanamine fumarate can have an endothermic initiation temperature of 179.47±3° C. and exhibit a maximum endothermic peak at an endothermic temperature of 189.05±3° C. in a differential scanning calorimetry analysis.

The crystalline form II of 1-(5-(2,4-difluorophenyl)-1-((3-fluorophenyl)sulfonyl)-4-methoxy-1H-pyrrol-3-yl)-N-methylmethanamine fumarate can be prepared by a polymorphic transition method through the phase transition from a crystalline form I of fumarate to a crystalline form II of fumarate.

For example, the crystalline form II of 1-(5-(2,4-difluorophenyl)-1-((3-fluorophenyl)sulfonyl)-4-methoxy-1H-pyrrol-3-yl)-N-methylmethanamine fumarate can be prepared by a solvent-mediated polymorphic transition method comprising the steps of:

1) dissolving a crystalline form I of 1-(5-(2,4-difluorophenyl)-1-((3-fluorophenyl)sulfonyl)-4-methoxy-1H-pyrrol-3-yl)-N-methylmethanamine fumarate in a $C_{1-8}$ aliphatic alcohol to prepare a solution; and 2) stirring the solution to subjecting the crystalline form I of 1-(5-(2,4-difluorophenyl)-1-((3-fluorophenyl)sulfonyl)-4-methoxy-1H-pyrrol-3-yl)-N-methylmethanamine fumarate to a polymorphic transition.

The step 1) is a step of preparing a solution using a good solvent capable of completely dissolving the crystalline form I, and may be performed at room temperature.

In this case, methanol, ethanol, propanol, isopropanol, n-butanol, or n-octanol may be used as the $C_{1-8}$ aliphatic alcohol. Preferably, ethanol may be used as the $C_{1-8}$ aliphatic alcohol.

The solvent may be used as a volume (ml/g) of 1-20 times, or preferably as a volume (ml/g) of 5-20 times, relative to the weight of the crystalline form I.

The step 2) is a step of stirring the solution prepared in the step 1) and changing a crystal structure of the crystalline form I in the solution to transit it to the crystalline form II, wherein the stirring is carried out at a temperature of 24° C. to 28° C. at a speed of 50 rpm to 300 rpm for 12 hours to 16 hours.

Alternatively, the crystalline form II of 1-(5-(2,4-difluorophenyl)-1-((3-fluorophenyl)sulfonyl)-4-methoxy-1H-pyrrol-3-yl)-N-methylmethanamine fumarate can be prepared by a solid-state polymorphic transition method comprising the step of:

vacuum-drying the crystalline form I of 1-(5-(2,4-difluorophenyl)-1-((3-fluorophenyl)sulfonyl)-4-methoxy-1H-pyrrol-3-yl)-N-methylmethanamine fumarate at 40° C. to 50° C. and subjecting it to a polymorphic transition.

The vacuum-drying in the above step can be carried out for 12 hours to 24 hours, and the crystal structure of the crystalline form I can be changed by the vacuum-drying to produce a crystalline form II.

The crystal produced by the polymorphic transition method can be recovered from the solution by a vacuum filtration process. If necessary, the recovered crystal may be washed and dried under vacuum to obtain a crystalline form having a high purity. In addition, the reaction conditions such as the ratio of solvent, the temperature range and the process time described in the above preparation methods can be adjusted depending on the selected solvent.

On the other hand, the present invention provides a pharmaceutical composition comprising: one or more crystalline forms selected from the group consisting of a crystalline form I of hydrochloride, a crystalline form II of hydrochloride, a crystalline form of succinate, a crystalline form of tartrate, a crystalline form I of fumarate and a crystalline form II of fumarate of 1-(5-(2,4-difluorophenyl)-1-((3-fluorophenyl)sulfonyl)-4-methoxy-1H-pyrrol-3-yl)-N-methylmethanamine.

Such pharmaceutical composition may include pharmaceutically acceptable carriers that are commonly used. The carrier be one that is usually used at the time of formulation, and it includes lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil and the like, but are not limited thereto. The pharmaceutical composition may further include a lubricant, a wetting agent, a sweetener, a flavoring agent, an emulsifying agent, a suspending agent, a preservative, etc. in addition to the above components.

The pharmaceutical composition may be administered orally, or administered parenterally, including intravenous, intramuscular, intraperitoneal, subcutaneous and transdermal routes of administration.

In this case, the pharmaceutical composition may be administered in a therapeutically effective amount, for example, in an effective amount ranging about 0.001 mg/kg to about 100 mg/kg per day. The dosage may vary depending on formulation method, administration method, patient's age, body weight, sexually transmitted infection, diet, administration time, administration route, excretion rate or susceptibility.

The pharmaceutical composition can be formulated by the method that can be performed easily by those in the art by using a pharmaceutically acceptable carrier and/or excipient in the form of unit dose or in multi-dose container. In this case, the formulations can be used without limitation as long as it is in any form suitable for pharmaceutical preparations including oral dosage forms such as powders, granules, tablets, capsules, suspensions, emulsions, syrups or aerosols, external preparations such as ointments or creams, suppositories and sterilized injection solutions. In addition, a dispersing agent or a stabilizer can be further included.

Advantageous Effects

The novel crystalline forms of 1-(5-(2,4-difluorophenyl)-1-((3-fluorophenyl)sulfonyl)-4-methoxy-1H-pyrrol-3-yl)-N-methylmethanamine salts according to the present invention have high solubility in water and excellent stability under moisture-proof conditions and high-humidity exposure conditions, and thus can be pharmaceutically used.

DETAILED DESCRIPTION OF THE EMBODIMENTS

Figure 1:
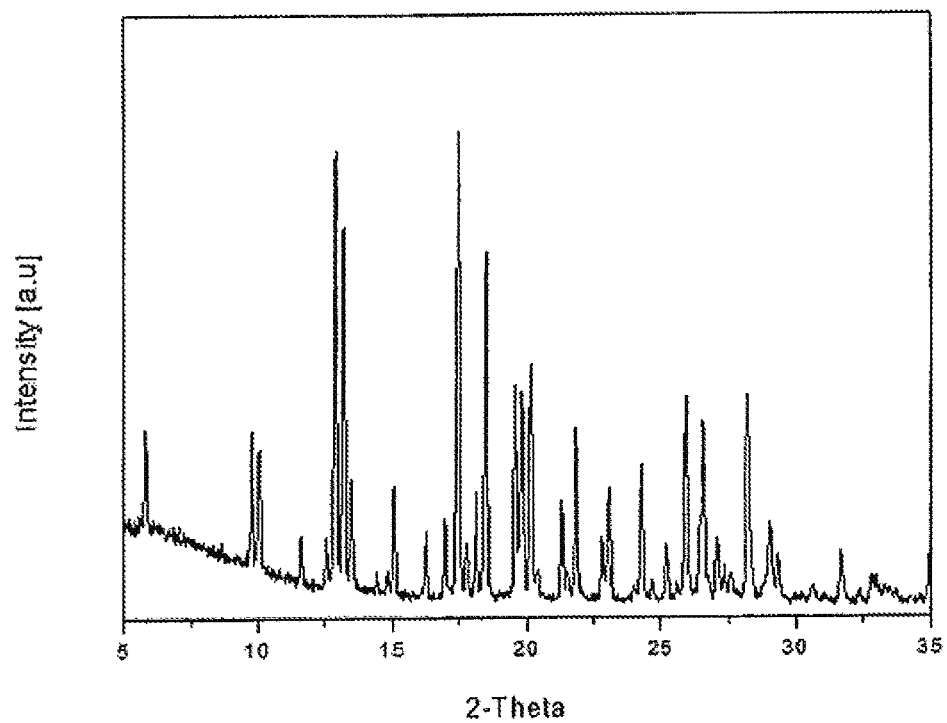
FIG. 1 shows an X-ray powder diffraction pattern of the crystalline form I of 1-(5-(2,4-difluorophenyl)-1-((3-fluorophenyl)sulfonyl)-4-methoxy-1H-pyrrol-3-yl)-N-methylmethanamine hydrochloride prepared in Example 1-1.

Below, preferred embodiments will be provided in order to assist in the understanding of the present disclosure. However, these examples are provided only for illustration of the present invention, and should not be construed as limiting the present invention to these examples.

Preparation Example 1: Preparation of 1-(5-(2,4-difluorophenyl)-1-((3-fluorophenyl)sulfonyl)-4-methoxy-1H-pyrrol-3-yl)-N-methylmethanamine (Free Base)

Step 1-1) Preparation of 2-(2,4-difluorophenyl)-2-((3-methoxy-2-(methoxycarbonyl)-3-oxoprop-1-en-1-yl)amino)acetic acid 2,4-Difluorophenyl glycine (150.0 g, 801.5 mmol), dimethyl 2-(methoxymethylene)malonate (126.9 g, 728.6 mmol) and sodium acetate (65.8 g, 801.5 mmol) were added to methanol (800.0 ml), and the mixture was then refluxed at 60° C. for 4 hours. The reaction mixture was cooled to room temperature and then concentrated under reduced pressure to remove about 70% of methanol, and then filtered. The obtained solid was dried under reduced pressure to give 190.0 g of the title compound. (Yield: 79.2%).

$^1$H-NMR (500 MHz, CDCl$_3$): 8.02-7.99 (m, 1H), 7.45-7.40 (m, 1H), 7.00-6.95 (m, 2H), 5.16 (s, 1H), 3.74 (s, 3H), 3.76 (s, 3H)

Step 1-2) Preparation of methyl 5-(2,4-difluorophenyl)-4-hydroxy-1H-pyrrol-3-carboxylate Acetic anhydride (1731.2 ml) and triethylamine (577.1 ml) were added to 2-(2,4-difluorophenyl)-2-((3-methoxy-2-

(methoxycarbonyl)-3-oxoprop-1-en-1-yl)amino)acetic acid (190.0 g, 577.1 mmol) prepared in the step 1-1. The reaction mixture was refluxed at 140° C. for 30 minutes and then cooled to 0° C. To the reaction mixture, ice water (577.1 ml) was added at 0° C., stirred at room temperature for 1 hours and then extracted with ethyl acetate. The obtained extract was dried over anhydrous magnesium sulfate, and concentrated under reduced pressure. The resulting compound was filtered using silica gel to remove solids, and then concentrated under reduced pressure.

Tetrahydrofuran (140.0 ml) and water (120.0 ml) were added to the resulting residue, and the mixture was cooled at 0° C. and sodium hydroxide (46.17 g, 1154.2 mmol) was then added thereto. The reaction mixture was stirred at 0° C. for 30 minutes, neutralized with 1N aqueous hydrochloric acid solution and then extracted with ethyl acetate. The obtained extract was dried over anhydrous magnesium sulfate, and then concentrated under reduced pressure. The resulting residue was purified by silica gel column chromatography (ethyl acetate:n-hexane=1:4 (v/v)) to give 22.0 g of the title compound. (Yield: 15.1%).

$^1$H-NMR (500 MHz, CDCl$_3$): 8.80 (s, 1H), 8.17-8.12 (m, 2H), 7.13 (d, 1H), 6.95 (t, 1H), 6.86-6.83 (m, 1H), 3.88 (s, 3H)

Step 1-3) Preparation of methyl 5-(2,4-difluorophenyl)-4-methoxy-1H-pyrrol-3-carboxylate Methyl 5-(2,4-difluorophenyl)-4-hydroxy-1H-pyrrol-3-carboxylate (22.0 g, 86.9 mmol) prepared in the step 1-2 was dissolved in tetrahydrofuran (434.5 ml) and methanol (173.9 ml). To the reaction mixture, (trimethylsilyl)diazomethane (2.0 M diethyl ether solution, 173.8 ml) was added, and stirred at room temperature for 48 hours. Water was added to the reaction mixture and extracted with ethyl acetate. The obtained extract was dried over anhydrous magnesium sulfate, and concentrated under reduced pressure. The resulting residue was purified by silica gel column chromatography (ethyl acetate:n-hexane=1:4 (v/v)) to give 18.1 g of the title compound. (Yield: 75.3%)

$^1$H-NMR (500 MHz, CDCl$_3$): 8.78 (s, 1H), 8.12 (m, 1H), 7.30 (d, 1H), 6.95 (t, 1H), 6.88 (t, 1H), 3.87 (s, 3H), 3.85 (s, 3H)

Step 1-4) Preparation of methyl 5-(2,4-difluorophenyl)-4-methoxy-1-((3-fluorophenyl)sulfonyl)-1H-pyrrol-3-carboxylate Methyl 5-(2,4-difluorophenyl)-4-methoxy-1H-pyrrol-3-carboxylate (18.0 g, 67.4 mmol) prepared in the step 1-3 was dissolved in dimethylformamide (335.0 ml). To the obtained solution, sodium hydride (60%, dispersion in liquid paraffin) (4.0 g, 101.0 mmol) was added at room temperature and the mixture was stirred at room temperature for 10 minutes. To the reaction mixture, 3-fluorobenzenesulfonyl chloride (13.37 ml, 101.0 mmol) was added, and the mixture was stirred at room temperature for 1 hour. Water was added to the reaction mixture and extracted with ethyl acetate. The obtained extract was dried over anhydrous magnesium sulfate, and then concentrated under reduced pressure. The resulting residue was purified by silica gel column chromatography (ethyl acetate:n-hexane=1:4 (v/v)) to give the title compound (26.1 g). (Yield: 91.1%).

$^1$H-NMR (500 MHz, CDCl$_3$): 7.98 (s, 1H), 7.43-7.39 (m, 1H), 7.30 (t, 1H), 7.23 (d, 1H), 7.15 (q, 1H), 7.67 (q, 1H), 6.91 (t, 1H), 6.77 (t, 1H), 3.87 (s, 3H), 3.61 (s, 3H)

Step 1-5) Preparation of 5-(2,4-difluorophenyl)-4-methoxy-1-((3-fluorophenyl)sulfonyl)-1H-pyrrol-3-carbaldehyde Methyl 5-(2,4-difluorophenyl)-4-methoxy-1-((3-fluorophenyl)sulfonyl)-1H-pyrrol-3-carboxylate (26.0 g, 61.1 mmol) prepared in the step 1-4 was dissolved in tetrahydrofuran (300.0 ml). Diisobutyl aluminum hydride (1.0 M tetrahydrofuran solution) (183.4 ml, 183.4 mmol) was added to the obtained solution at 0° C., and the mixture was stirred at room temperature for 1 hour, neutralized with 1N hydrochloric acid solution and then extracted with ethylacetate. The obtained extract was dried over anhydrous magnesium sulfate, and then concentrated under reduced pressure.

The resulting residue was dissolved in dichloromethane (300.0 ml), and then celite (26.0 g) and pyridinium chlorochromate (39.5 g, 183.4 mmol) were added thereto. The reaction mixture was stirred at room temperature for 1 hour and then filtered to remove a solid, and the obtained filtrate was concentrated under reduced pressure. The resulting residue was purified by silica gel column chromatography (ethyl acetate:n-hexane=1:2 (v/v)) to give the title compound (17.2 g). (Yield: 70.9%).

$^1$H-NMR (500 MHz, CDCl$_3$): 9.89 (s, 1H), 7.99 (s, 1H), 7.45-7.41 (m, 1H), 7.33 (s, 1H), 7.25 (d, 1H), 7.18 (q, 1H), 7.05 (s, 1H), 6.92 (t, 1H), 6.77 (t, 1H), 3.63 (s, 3H)

Step 1-6) Preparation of 1-(5-(2,4-difluorophenyl)-4-methoxy-1-((3-fluorophenyl)sulfonyl)-1H-pyrrol-3-yl)-N-methylmethanamine 5-(2,4-difluorophenyl)-4-methoxy-1-((3-fluorophenyl)sulfonyl)-1H-pyrrol-3-carbaldehyde (17.0 g, 43.0 mmol) prepared in the step 1-5 was dissolved in methanol (430.0 ml). Methylamine (9.8 M methanol solution) (87.8 ml, 860.0 mmol) was added to the obtained solution, and the mixture was stirred at room temperature for 30 minutes. Sodium borohydride (16.3 g, 430.0 mmol) was added to the reaction mixture, and the mixture was stirred at room temperature for 30 minutes. Water was added to the reaction mixture and extracted with ethyl acetate. The obtained extract was dried over anhydrous magnesium sulfate, and then concentrated under reduced pressure. The resulting residue was purified by silica gel column chromatography (ethyl acetate:n-hexane=1:2 (v/v)) to give the title compound (15.2 g). (Yield: 86.1%).

$^1$H-NMR (500 MHz, CDCl$_3$): 7.39-7.35 (m, 1H), 7.26-7.20 (m, 2H), 7.15 (q, 1H), 7.06 (d, 1H), 6.87 (t, 1H), 6.78 (t, 1H), 3.60 (d, 2H), 3.44 (s, 3H), 2.45 (s, 3H)

Preparation Example 2: Preparation of 1-(5-(2,4-difluorophenyl)-1-((3-fluorophenyl)sulfonyl)-4-methoxy-1H-pyrrol-3-yl)-N-methylmethanamine hydrochloride

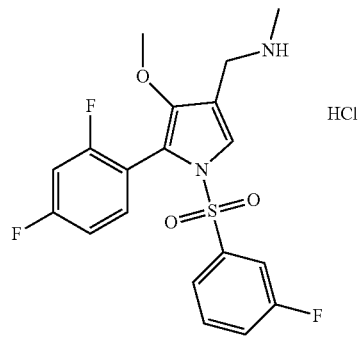 [SMILES: CNCc1cn(S(=O)(=O)c2cccc(F)c2)c(-c2ccc(F)cc2F)c1OC ; Cl]

1-(5-(2,4-difluorophenyl)-1-((3-fluorophenyl)sulfonyl)-4-methoxy-1H-pyrrol-3-yl)-N-methyl methanamine (15.0 g, 36.6 mmol) prepared in Preparation Example 1 was dissolved in ethyl acetate (36.6 ml) to which hydrochloric acid solution (2.0 M diethyl ether solution) (36.6 ml, 73.1 mmol) was added. The reaction mixture was stirred at room temperature for 1 hour and then filtered, and the obtained solid was dried under reduced pressure to give the title compound (15.1 g). (Yield: 92.5%).

Molecular weight 446.87

$^1$H-NMR (500 MHz, MeOD): 7.69 (s, 1H), 7.58-7.53 (m, 1H), 7.45 (t, 1H), 7.30 (d, 1H), 7.20-7.15 (m, 2H), 7.02-6.94 (m, 2H), 4.07 (d, 2H), 3.46 (s, 3H), 2.71 (s, 3H)

Hereinafter, in the following examples, 1-(5-(2,4-difluorophenyl)-4-methoxy-1-((3-fluorophenyl)sulfonyl)-1H-pyrrol-3-yl)-N-methylmethanamine (free base) prepared in Preparation Example 1 and 1-(5-(2,4-difluorophenyl)-1-((3-fluorophenyl)sulfonyl)-4-methoxy-1H-pyrrol-3-yl)-N-methyl methanamine hydrochloride prepared in Preparation Example 2 were used.

Example 1-1: Preparation of Crystalline Form I of Hydrochloride by an Evaporative Crystallization Method 300 mg of 1-(5-(2,4-difluorophenyl)-1-((3-fluorophenyl) sulfonyl)-4-methoxy-1H-pyrrol-3-yl)-N-methylmethanamine hydrochloride was dissolved in 5 ml of ethanol to prepare a solution. Then, ethanol was evaporated from the prepared solution at room temperature for 1 day. After a crystal was produced, the crystal was separated by filtration under reduced pressure to obtain 250 mg of crystalline form I of 1-(5-(2,4-difluorophenyl)-1-((3-fluorophenyl)sulfonyl)-4-methoxy-1H-pyrrol-3-yl)-N-methylmethanamine hydrochloride.

Example 1-2: Preparation of Crystalline Form I of Hydrochloride by a Drowning-Out Crystallization Method 300 mg of 1-(5-(2,4-difluorophenyl)-1-((3-fluorophenyl) sulfonyl)-4-methoxy-1H-pyrrol-3-yl)-N-methylmethanamine hydrochloride was dissolved in 5 ml of ethanol to prepare a solution. Then, 5 ml of n-hexane was added to the prepared solution and stirred at 50 rpm at room temperature for 1 day. After a crystal was produced, the crystal was separated by filtration under reduced pressure to obtain 235 mg of crystalline form I of 1-(5-(2,4-difluorophenyl)-1-((3-fluorophenyl)sulfonyl)-4-methoxy-1H-pyrrol-3-yl)-N-methylmethanamine hydrochloride.

Example 2: Preparation of Crystalline Form II of Hydrochloride by an Evaporative Crystallization Method 20 mg of 1-(5-(2,4-difluorophenyl)-1-((3-fluorophenyl) sulfonyl)-4-methoxy-1H-pyrrol-3-yl)-N-methylmethanamine hydrochloride was dissolved in 1 ml of methanol to prepare a solution. Then, methanol was evaporated from the prepared solution at room temperature for 1 day. After a crystal was produced, the crystal was separated by filtration under reduced pressure to obtain 15 mg of crystalline form II of 1-(5-(2,4-difluorophenyl)-1-((3-fluorophenyl)sulfonyl)-4-methoxy-1H-pyrrol-3-yl)-N-methylmethanamine hydrochloride.

Example 3-1: Preparation of Crystalline Form of Succinate by an Evaporative Crystallization Method 300 mg of 1-(5-(2,4-difluorophenyl)-1-((3-fluorophenyl) sulfonyl)-4-methoxy-1H-pyrrol-3-yl)-N-methylmethanamine free base and 86.3 mg of succinic acid were dissolved in 5 ml of methanol to prepare a solution. Then, methanol was evaporated from the prepared solution at room temperature for 2 days. After a crystal was produced, the crystal was separated by filtration under reduced pressure to obtain 340 mg of crystalline form of 1-(5-(2,4-difluorophenyl)-1-((3-fluorophenyl)sulfonyl)-4-methoxy-1H-pyrrol-3-yl)-N-methylmethanamine succinate.

Example 3-2: Preparation of Crystalline Form of Succinate by a Drowning-Out Crystallization Method 300 mg of 1-(5-(2,4-difluorophenyl)-1-((3-fluorophenyl) sulfonyl)-4-methoxy-1H-pyrrol-3-yl)-N-methylmethanamine free base and 86.3 mg of succinic acid were dissolved in 5 ml of methanol to prepare a solution. Then, 5 ml of n-hexane was added to the prepared solution and stirred at 50 rpm at room temperature for 4 hours. After a crystal was produced, the crystal was separated by filtration under reduced pressure to obtain 300 mg of crystalline form of 1-(5-(2,4-difluorophenyl)-1-((3-fluorophenyl)sulfonyl)-4-methoxy-1H-pyrrol-3-yl)-N-methylmethanamine succinate.

Example 4-1: Preparation of Crystalline Form of Tartrate by an Evaporative Crystallization Method 300 mg of 1-(5-(2,4-difluorophenyl)-1-((3-fluorophenyl) sulfonyl)-4-methoxy-1H-pyrrol-3-yl)-N-methyl methanamine free base and 109.7 mg of tartaric acid were dissolved in 5 ml of methanol to prepare a solution. Then, methanol was evaporated from the prepared solution at room temperature for 2 days. After a crystal was produced, the crystal was separated by filtration under reduced pressure to obtain 385 mg of crystalline form of 1-(5-(2,4-difluorophenyl)-1-((3-fluorophenyl)sulfonyl)-4-methoxy-1H-pyrrol-3-yl)-N-methylmethanamine tartrate.

Example 4-2: Preparation of Crystalline Form of Tartrate by a Drowning-Out Crystallization Method 300 mg of 1-(5-(2,4-difluorophenyl)-1-((3-fluorophenyl) sulfonyl)-4-methoxy-1H-pyrrol-3-yl)-N-methylmethanamine free base and 109.7 mg of tartaric acid were dissolved in 5 ml of ethanol to prepare a solution. Then, 5 ml of n-hexane was added to the prepared solution and stirred at 50 rpm at room temperature for 4 hours. After a crystal was produced, the crystal was separated by filtration under reduced pressure to obtain 340 mg of crystalline form of 1-(5-(2,4-difluorophenyl)-1-((3-fluorophenyl)sulfonyl)-4-methoxy-1H-pyrrol-3-yl)-N-methylmethanamine tartrate.

Example 5-1: Preparation of Crystalline Form I of Fumarate by an Evaporative Crystallization Method 300 mg of 1-(5-(2,4-difluorophenyl)-1-((3-fluorophenyl) sulfonyl)-4-methoxy-1H-pyrrol-3-yl)-N-methyl methanamine free base and 84.8 mg of fumaric acid were dissolved in 5 ml of ethanol to prepare a solution. Then, ethanol was evaporated from the prepared solution at room temperature for 2 days. After a crystal was produced, the crystal was separated by filtration under reduced pressure to obtain 340 mg of crystalline form I of 1-(5-(2,4-difluorophenyl)-1-((3-fluorophenyl)sulfonyl)-4-methoxy-1H-pyrrol-3-yl)-N-methyl methanamine fumarate.

Example 5-2: Preparation of Crystalline Form I of Fumarate by a Reactive Crystallization Method 300 mg of 1-(5-(2,4-difluorophenyl)-1-((3-fluorophenyl) sulfonyl)-4-methoxy-1H-pyrrol-3-yl)-N-methyl methanamine free base was dissolved in 5 ml of ethanol, and 109.7 mg of fumaric acid was dissolved in 3 ml of ethanol to prepare respective solutions. Then, the prepared two solutions were mixed and stirred at 50 rpm for 2 hours at room temperature. After a crystal was produced, the crystal was separated by filtration under reduced pressure to obtain 314 mg of crystalline form I of 1-(5-(2,4-difluorophenyl)-1-((3-fluorophenyl)sulfonyl)-4-methoxy-1H-pyrrol-3-yl)-N-methylmethanamine fumarate.

Example 6-1: Preparation of Crystalline Form II of Fumarate by a Solvent-Mediated Polymorphic Transition Method 300 mg of crystalline form I of 1-(5-(2,4-difluorophenyl)-1-((3-fluorophenyl)sulfonyl)-4-methoxy-1H-pyrrol-3-yl)-N-methyl methanamine fumarate was dissolved in 5 ml of ethanol to prepare a solution. Then, the prepared solution was stirred at 50 rpm at room temperature for 16 hours. After a crystal was produced, the crystal was separated by filtration under reduced pressure to obtain 250 mg of crystalline form II of 1-(5-(2,4-difluorophenyl)-1-((3-fluorophenyl) sulfonyl)-4-methoxy-1H-pyrrol-3-yl)-N-methylmethanamine fumarate

Example 6-2: Preparation of Crystalline Form II of Fumarate by a Solid-State Polymorphic Transition Method 300 mg of crystalline form I of 1-(5-(2,4-difluorophenyl)-1-((3-fluorophenyl)sulfonyl)-4-methoxy-1H-pyrrol-3-yl)-N-methyl methanamine fumarate was dried under vacuum at a temperature of 50° C. for 24 hours. After a crystal was produced, the crystal was separated by filtration under reduced pressure to obtain 300 mg of crystalline form II of 1-(5-(2,4-difluorophenyl)-1-((3-fluorophenyl)sulfonyl)-4-methoxy-1H-pyrrol-3-yl)-N-methyl methanamine fumarate

Comparative Example 1: Preparation of Crystalline Form of Free Base by a Cooling Crystallization Method 100 mg of 1-(5-(2,4-difluorophenyl)-1-((3-fluorophenyl) sulfonyl)-4-methoxy-1H-pyrrol-3-yl)-N-methylmethanamine free base was cooled at a low temperature of 4° C. for 2 weeks. After a crystal was produced, the crystal was separated by filtration under reduced pressure to obtain 100 mg of crystalline form of 1-(5-(2,4-difluorophenyl)-1-((3-fluorophenyl)sulfonyl)-4-methoxy-1H-pyrrol-3-yl)-N-methyl methanamine free base.

Test Example 1: Inhibitory Effects on Proton Pump ($H_+/K_+$-ATPase) Activity The inhibitory effects on proton pump ($H_+/K_+$-ATPase) activity of 1-(5-(2,4-difluorophenyl)-1-((3-fluorophenyl) sulfonyl)-4-methoxy-1H-pyrrol-3-yl)-N-methylmethanamine hydrochloride prepared in Preparation Example 2 were measured as follows.

Gastric vesicles were prepared from a hog stomach according to a known method (Edd C. Rabon et al., Preparation of Gastric $H_+,K_+$-ATPase., Methods in enzymology, vol. 157 Academic Press Inc., (1988), pp. 649-654). The protein contents of gastric vesicles thus prepared were quantitatively measured with Bicinchoninic Acid (BCA) kit (Thermo). 80 ul of (a predetermined concentration of a test compound, 0.5% DMSO, 2.5 mM $MgCl_2$, 12.5 mM KCl, 1.25 mM EDTA, 60 mM Tris-HCl, pH7.4) was added to each well of 96-well plates. 10 µl of a reaction solution containing gastric vesicles (60 mmol/l, Tris-HCl buffer, pH 7.4) and 10 µl of a Tris buffer solution containing adenosine triphosphate (10 mM ATP, Tris-HCl buffer solution, pH 7.4) were added to each well and subjected to enzymatic reaction at 37° C. for 40 minutes. 50 µl of malachite green solution (0.12% malachite green solution in 6.2 N sulfuric acid, 5.8% ammonium molybdate and 11% Tween 20 were mixed at a ratio of 100:67:2) was added thereto to stop the enzyme reaction, and 50 µl of 15.1% sodium citrate was added thereto. The amount of monophosphate (Pi) in the reaction solution was measured at 570 nm by using a microplate reader (FLUOstar Omega, BMG). The inhibition rate (%) was measured from the activity value of the control group and the activity value of the test compounds at various concentrations. The concentration ($IC_{50}$) that inhibits $H_+/K_+$-ATPase activity by 50% was calculated from each % inhibition value of the compounds using Logistic 4-parameter function of Sigmaplot 8.0 program. As a result, 1-(5-(2,4-difluorophenyl)-1-((3-fluorophenyl)sulfonyl)-4-methoxy-1H-pyrrol-3-yl)-N-methylmethanamine hydrochloride prepared in Preparation Example 2 exhibited an $IC_{50}$ value of 0.024 µM. Thus, a salt of 1-(5-(2,4-difluorophenyl)-1-((3-fluorophenyl)sulfonyl)-4-methoxy-1H-pyrrol-3-yl)-N-methylmethanamine according to one embodiment of the present invention had excellent proton pump inhibitory activity and thus can be used for a pharmaceutical composition for the prevention and treatment of gastrointestinal injury due to gastrointestinal tract ulcer, gastritis, reflux esophagitis, or *H. pylori*.

Test Example 2: X-Ray Powder Diffraction Analysis

X-ray powder diffraction analysis was performed for the crystalline forms prepared in the Examples and Comparative Examples, and the results were shown in FIGS. 1 to 7. In this case, the X-ray powder diffraction analysis was carried out using a CuKα target in the range of diffraction angles (2θ) of 5° to 35° with an X-ray powder diffraction spectrometer (D8 Advance, Bruker) under conditions of a voltage of 45 kV, a current amount of 40 mA, a divergence and scattering slit of 1°, a light receiving slit of 0.2 mm, and a scanning speed of 3°/min (0.4 seconds/0.02° interval).

Referring to FIG. 1, it could be confirmed that the crystalline form I of 1-(5-(2,4-difluorophenyl)-1-((3-fluorophenyl)sulfonyl)-4-methoxy-1H-pyrrol-3-yl)-N-methylmethanamine hydrochloride prepared in Example 1-1 had peaks at diffraction angles (2θ) of 5.8°, 9.7°, 10.0°, 12.8°, 13.2°, 17.4°, 18.5°, 19.5°, 19.8°, 20.1°, 21.8°, 25.9°, 26.5° and 28.2° in an X-ray powder diffraction pattern.

Figure 2:
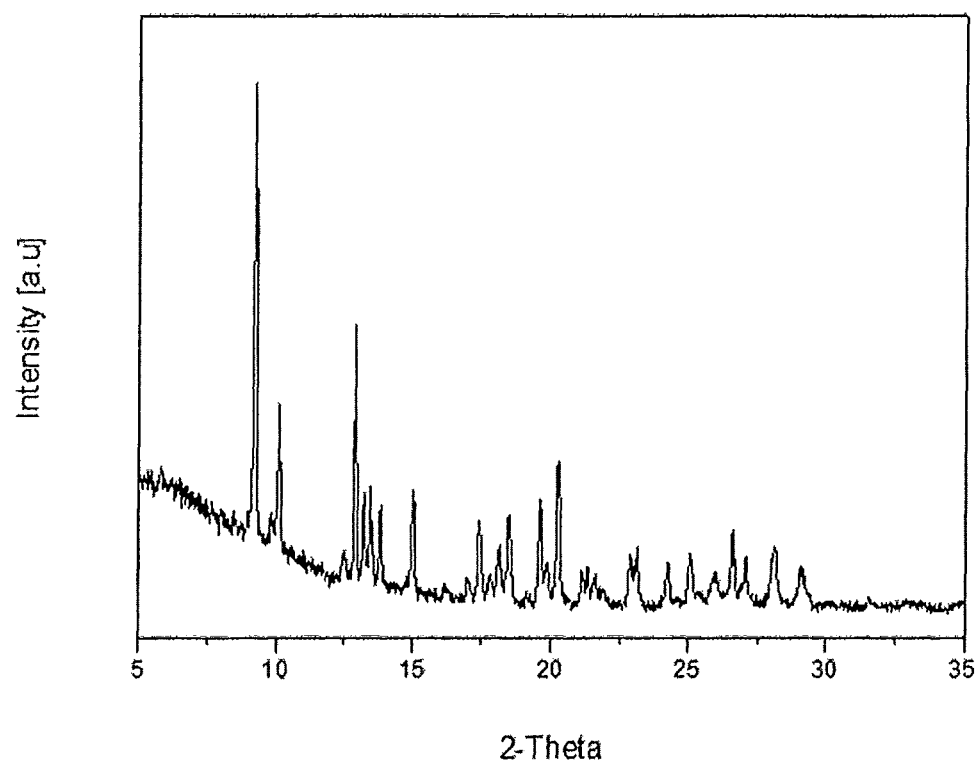
FIG. 2 shows an X-ray powder diffraction pattern of the crystalline form II of 1-(5-(2,4-difluorophenyl)-1-((3-fluorophenyl)sulfonyl)-4-methoxy-1H-pyrrol-3-yl)-N-methylmethanamine hydrochloride prepared in Example 2.

Referring to FIG. 2, it could be confirmed that the crystalline form II of 1-(5-(2,4-difluorophenyl)-1-((3-fluorophenyl)sulfonyl)-4-methoxy-1H-pyrrol-3-yl)-N-methylmethanamine hydrochloride prepared in Example 2 had peaks at diffraction angles (2θ) of 9.2°, 9.8°, 10.0°, 12.9°, 13.2°, 13.4°, 13.8°, 15.0°, 18.4°, 19.6° and 20.2° in an X-ray powder diffraction pattern.

Figure 3:
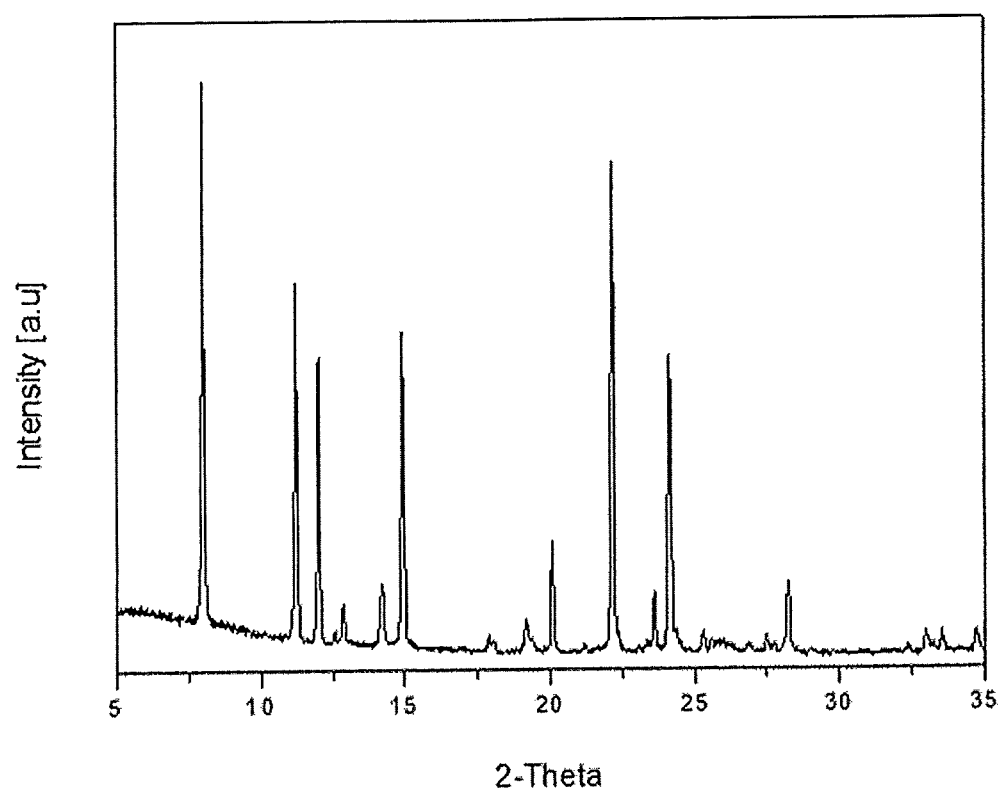
FIG. 3 shows an X-ray powder diffraction pattern of the crystalline form of 1-(5-(2,4-difluorophenyl)-1-((3-fluorophenyl)sulfonyl)-4-methoxy-1H-pyrrol-3-yl)-N-methylmethanamine succinate prepared in Example 3-1.

Referring to FIG. 3, it could be confirmed that the crystalline form of 1-(5-(2,4-difluorophenyl)-1-((3-fluorophenyl)sulfonyl)-4-methoxy-1H-pyrrol-3-yl)-N-methylmethanamine succinate prepared in Example 3-1 had peaks at diffraction angles (2θ) of 8.0°, 11.2°, 12.0°, 14.9°, 20.0°, 22.1° and 24.1° in an X-ray powder diffraction pattern.

Figure 4:
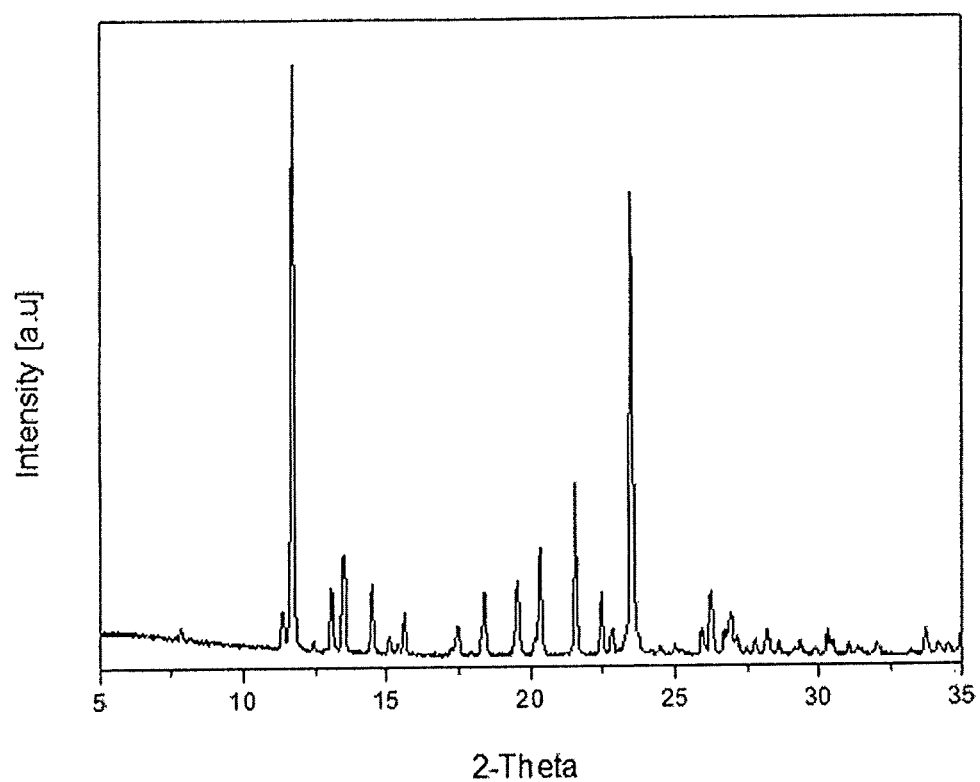
FIG. 4 shows an X-ray powder diffraction pattern of the crystalline form of 1-(5-(2,4-difluorophenyl)-1-((3-fluorophenyl)sulfonyl)-4-methoxy-1H-pyrrol-3-yl)-N-methylmethanamine tartrate prepared in Example 4-1.

Referring to FIG. 4, it could be confirmed that the crystalline form of 1-(5-(2,4-difluorophenyl)-1-((3-fluorophenyl)sulfonyl)-4-methoxy-1H-pyrrol-3-yl)-N-methylmethanamine tartrate prepared in Example 4-1 had peaks at diffraction angles (2θ) of 11.7°, 13.0°, 13.5°, 14.5°, 18.3°, 19.5°, 20.3°, 21.5° and 23.5° in an X-ray powder diffraction pattern.

Figure 5:
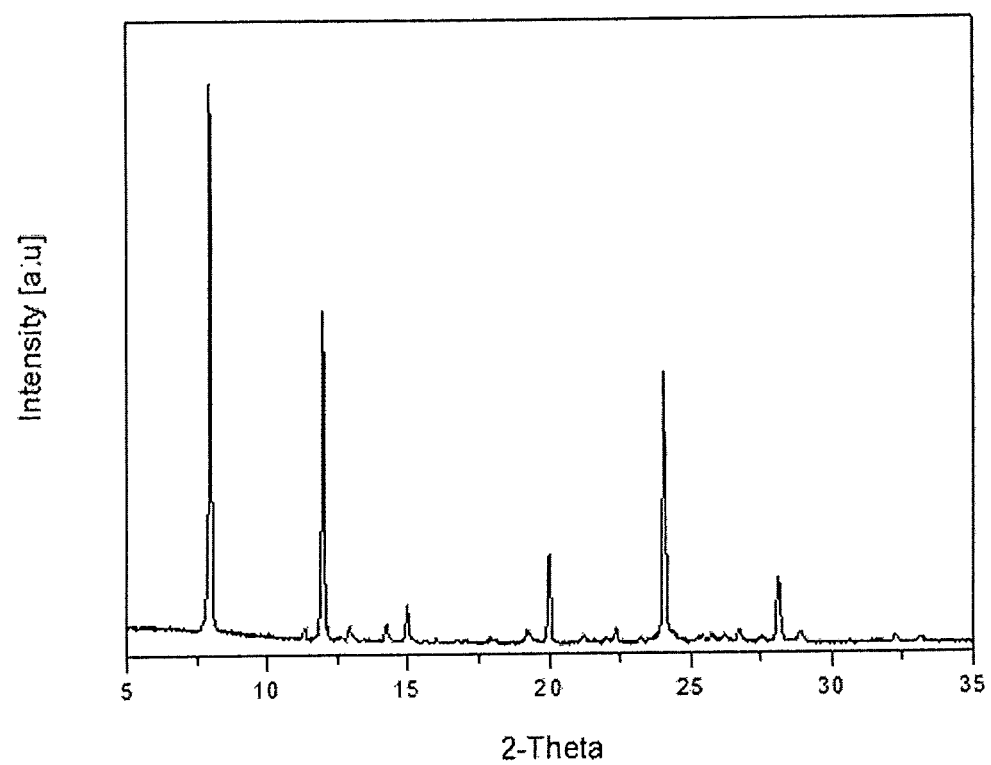
FIG. 5 shows an X-ray powder diffraction pattern of the crystalline form I of 1-(5-(2,4-difluorophenyl)-1-((3-fluorophenyl)sulfonyl)-4-methoxy-1H-pyrrol-3-yl)-N-methylmethanamine fumarate prepared in Example 5-1.

Referring to FIG. 5, it could be confirmed that the crystalline form I of 1-(5-(2,4-difluorophenyl)-1-((3-fluorophenyl)sulfonyl)-4-methoxy-1H-pyrrol-3-yl)-N-methylmethanamine fumarate prepared in Example 5-1 had peaks at diffraction angles (2θ) of 7.9°, 11.9°, 20.0° and 24.0° in an X-ray powder diffraction pattern.

Figure 6:
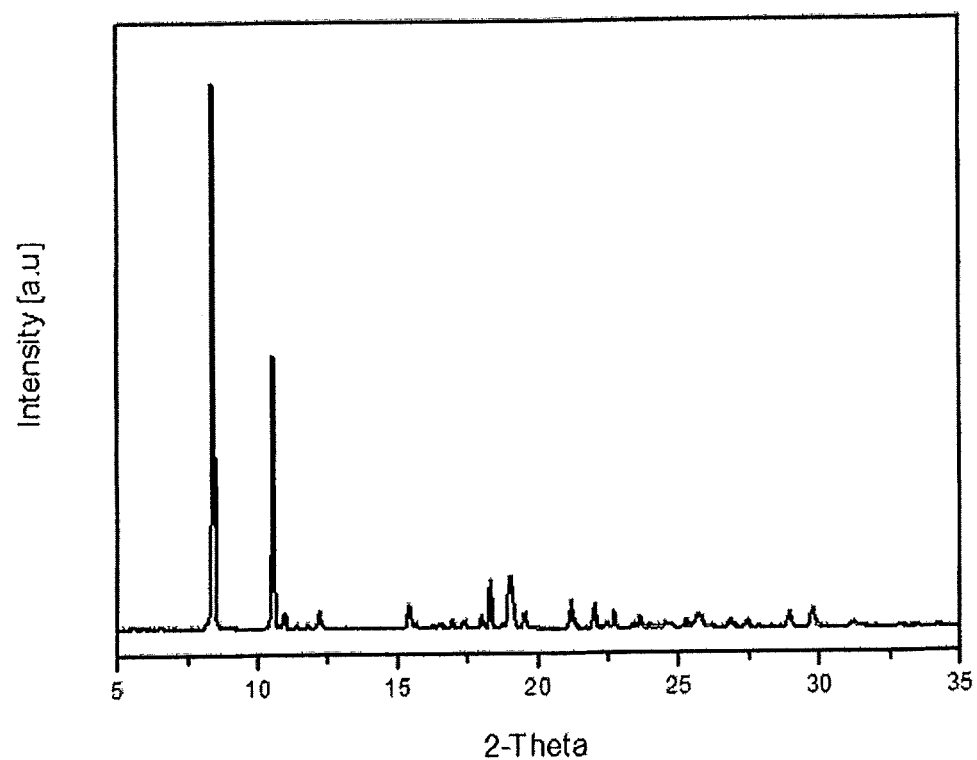
FIG. 6 shows an X-ray powder diffraction pattern of the crystalline form II of 1-(5-(2,4-difluorophenyl)-1-((3-fluorophenyl)sulfonyl)-4-methoxy-1H-pyrrol-3-yl)-N-methylmethanamine fumarate prepared in Example 6-1.

Referring to FIG. 6, it could be confirmed that the crystalline form II of 1-(5-(2,4-difluorophenyl)-1-((3-fluorophenyl)sulfonyl)-4-methoxy-1H-pyrrol-3-yl)-N-methylmethanamine fumarate prepared in Example 6-1 had peaks at diffraction angles (2θ) of 8.4°, 10.5°, 18.3° and 19.02° in an X-ray powder diffraction pattern.

Figure 7:
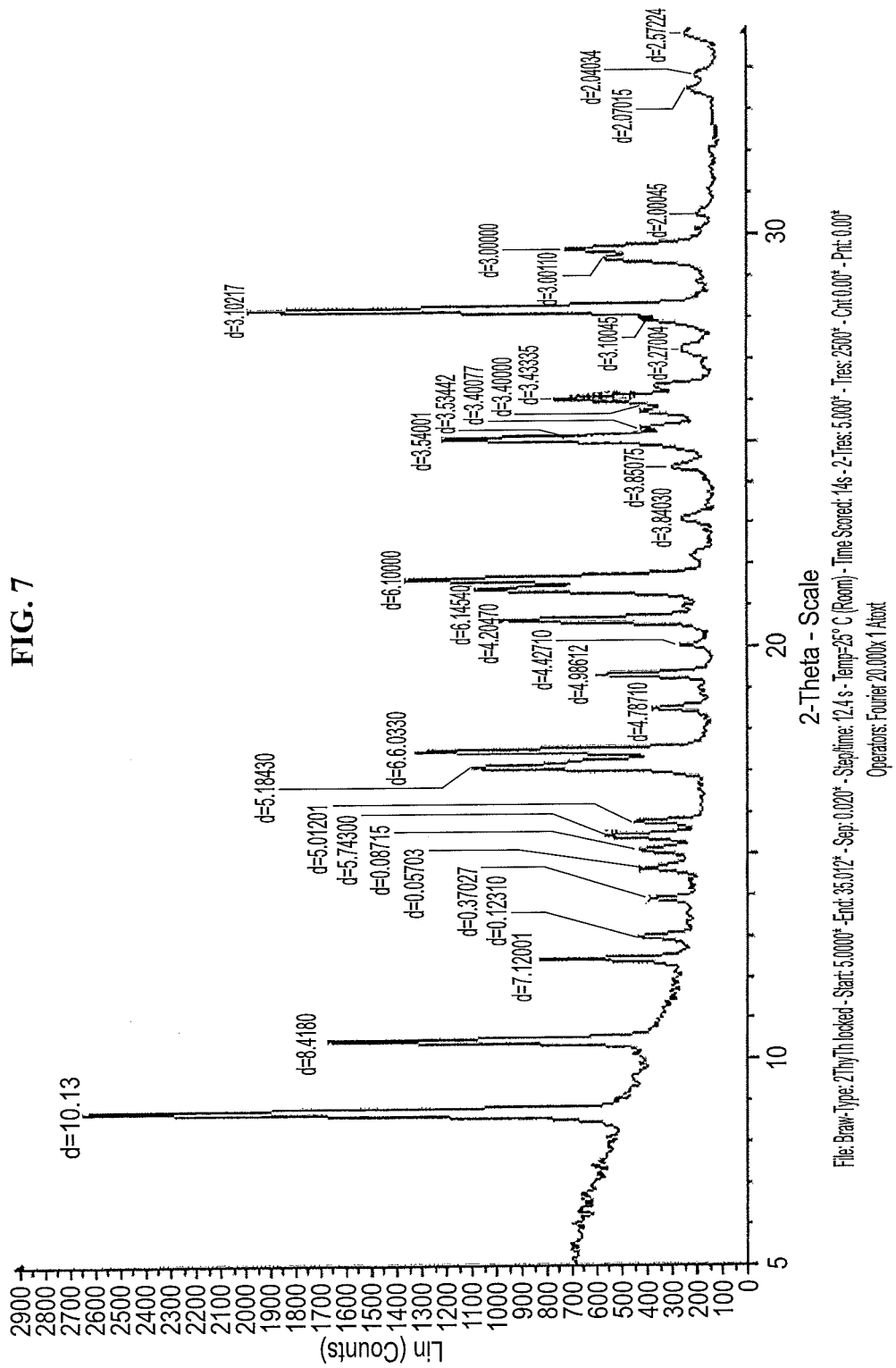
FIG. 7 shows an X-ray powder diffraction pattern of the crystalline form of 1-(5-(2,4-difluorophenyl)-1-((3-fluorophenyl)sulfonyl)-4-methoxy-1H-pyrrol-3-yl)-N-methylmethanamine free base prepared in Comparative Example 1.

Referring to FIG. 7, it could be confirmed that the crystalline form of 1-(5-(2,4-difluorophenyl)-1-((3-fluorophenyl)sulfonyl)-4-methoxy-1H-pyrrol-3-yl)-N-methylmethanamine free base prepared in Comparative Example 1 had peaks at diffraction angles (2θ) of 8.7°, 10.4°, 12.4°, 17.08°, 17.48°, 21.6°, 25.06°, 26.03°, 28.70 and 29.6° in an X-ray powder diffraction pattern.

Test Example 3: Differential Scanning Calorimetry Analysis

The differential scanning calorimetry analysis was carried out for the crystalline forms prepared in the Examples and Comparative Example and the results were shown in FIG. 8 to FIG. 14. In this case, the differential scanning calorimetry analysis was carried out with raising the temperature from 200° C. to 300° C. at a scanning rate of 10° C./min under a nitrogen purification in a sealed pan using a differential scanning calorimeter (DSC Q20, TA Instruments Co., Ltd.).

Figure 8:
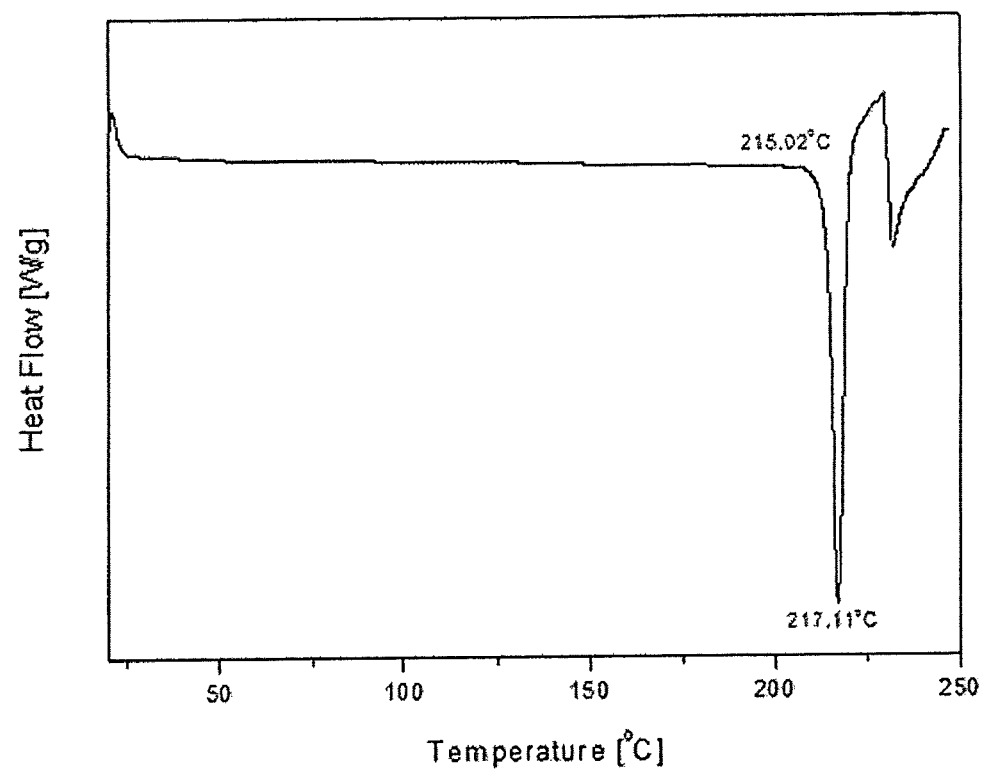
FIG. 8 shows a differential scanning calorimetry analysis result of the crystalline form I of 1-(5-(2,4-difluorophenyl)-1-((3-fluorophenyl)sulfonyl)-4-methoxy-1H-pyrrol-3-yl)-N-methylmethanamine hydrochloride prepared in Example 1-1.

Referring to FIG. 8, it could be confirmed that the crystalline form I of 1-(5-(2,4-difluorophenyl)-1-((3-fluorophenyl)sulfonyl)-4-methoxy-1H-pyrrol-3-yl)-N-methylmethanamine hydrochloride prepared in Example 1-1 had an endothermic initiation temperature of 215.02° C. and exhibited a maximum endothermic peak at an endothermic temperature of 217.11° C. in a differential scanning calorimetry analysis.

Figure 9:
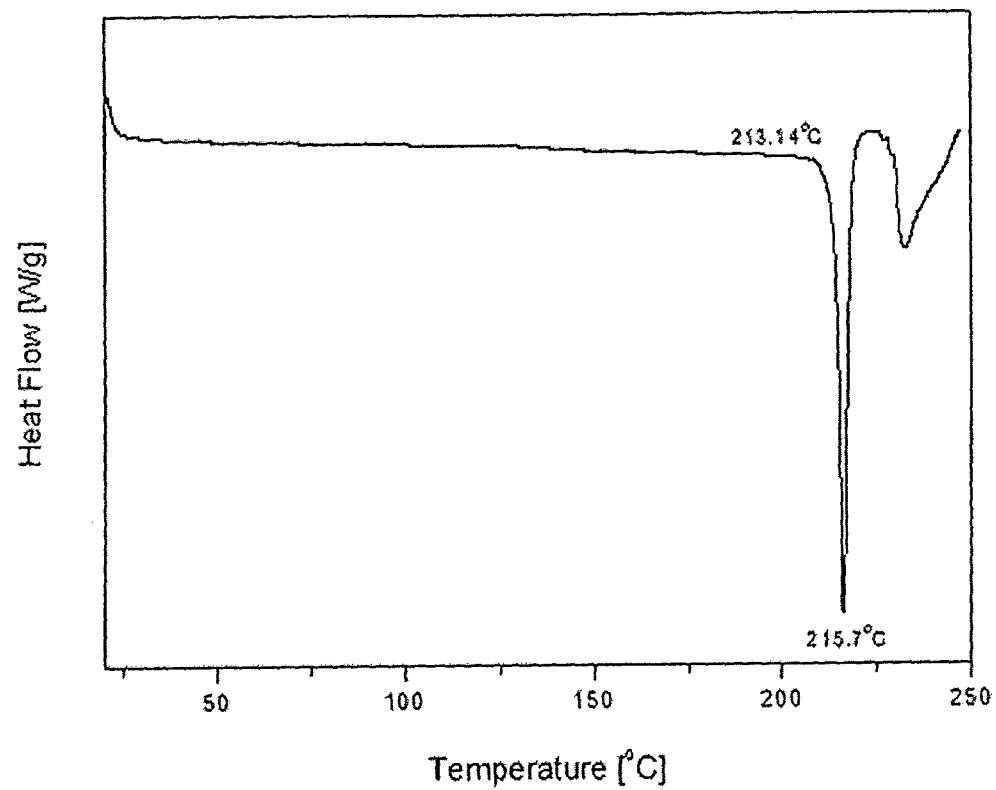
FIG. 9 shows a differential scanning calorimetry analysis result of the crystalline form II of 1-(5-(2,4-difluorophenyl)-1-((3-fluorophenyl)sulfonyl)-4-methoxy-1H-pyrrol-3-yl)-N-methylmethanamine hydrochloride prepared in Example 2.

Referring to FIG. 9, it could be confirmed that the crystalline form II of 1-(5-(2,4-difluorophenyl)-1-((3-fluorophenyl)sulfonyl)-4-methoxy-1H-pyrrol-3-yl)-N-methylmethanamine hydrochloride prepared in Example 2 had an endothermic initiation temperature of 213.14° C. and exhibited a maximum endothermic peak at an endothermic temperature of 215.7° C. in a differential scanning calorimetry analysis.

Figure 10:
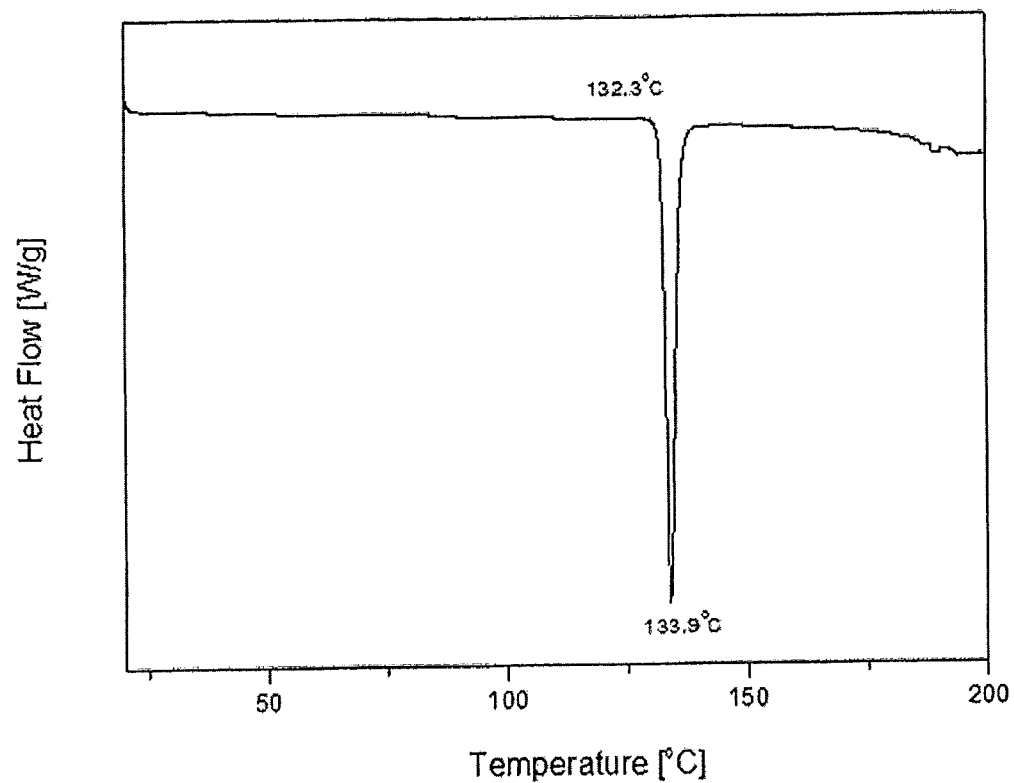
FIG. 10 shows a differential scanning calorimetry analysis result of the crystalline form of 1-(5-(2,4-difluorophenyl)-1-((3-fluorophenyl)sulfonyl)-4-methoxy-1H-pyrrol-3-yl)-N-methylmethanamine succinate prepared in Example 3-1.

Referring to FIG. 10, it could be confirmed that the crystalline form of 1-(5-(2,4-difluorophenyl)-1-((3-fluorophenyl)sulfonyl)-4-methoxy-1H-pyrrol-3-yl)-N-methylmethanamine succinate prepared in Example 3-1 had an endothermic initiation temperature of 132.3° C. and exhibited a maximum endothermic peak at an endothermic temperature of 133.9° C. in a differential scanning calorimetry analysis.

Figure 11:
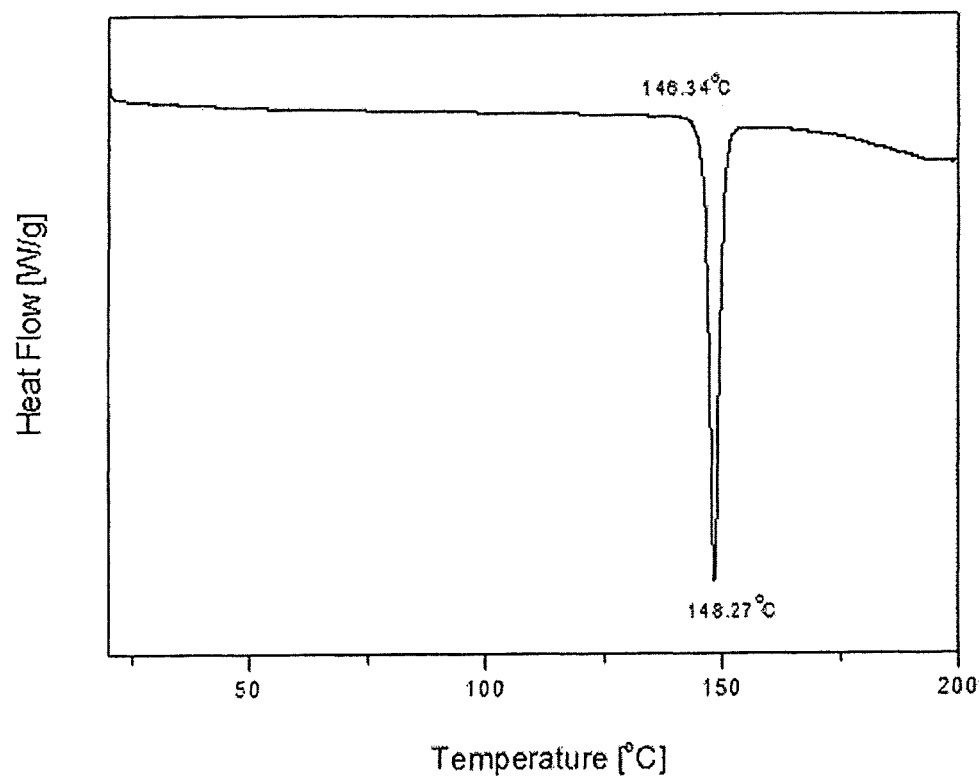
FIG. 11 shows a differential scanning calorimetry analysis result of the crystalline form of 1-(5-(2,4-difluorophenyl)-1-((3-fluorophenyl)sulfonyl)-4-methoxy-1H-pyrrol-3-yl)-N-methylmethanamine tartrate prepared in Example 4-1.

Referring to FIG. 11, it could be confirmed that the crystalline form of 1-(5-(2,4-difluorophenyl)-1-((3-fluorophenyl)sulfonyl)-4-methoxy-1H-pyrrol-3-yl)-N-methylmethanamine tartrate prepared in Example 4-1 had an endothermic initiation temperature of 146.34° C. and exhibited a maximum endothermic peak at an endothermic temperature of 148.27° C. in a differential scanning calorimetry analysis.

Figure 12:
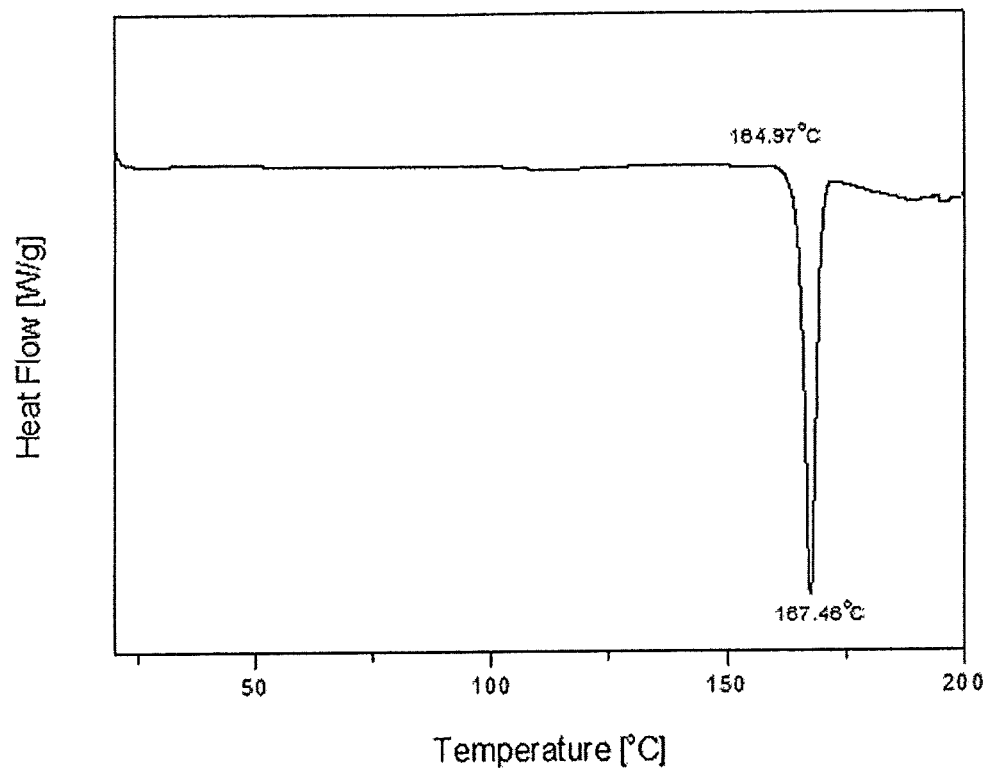
FIG. 12 shows a differential scanning calorimetry analysis result of the crystalline form I of 1-(5-(2,4-difluorophenyl)-1-((3-fluorophenyl)sulfonyl)-4-methoxy-1H-pyrrol-3-yl)-N-methylmethanamine fumarate prepared in Example 5-1.

Referring to FIG. 12, it could be confirmed that the crystalline form I of 1-(5-(2,4-difluorophenyl)-1-((3-fluorophenyl)sulfonyl)-4-methoxy-1H-pyrrol-3-yl)-N-methylmethanamine fumarate prepared in Example 5-1 had an endothermic initiation temperature of 164.97° C. and exhibited a maximum endothermic peak at an endothermic temperature of 167.46° C. in a differential scanning calorimetry analysis.

Figure 13:
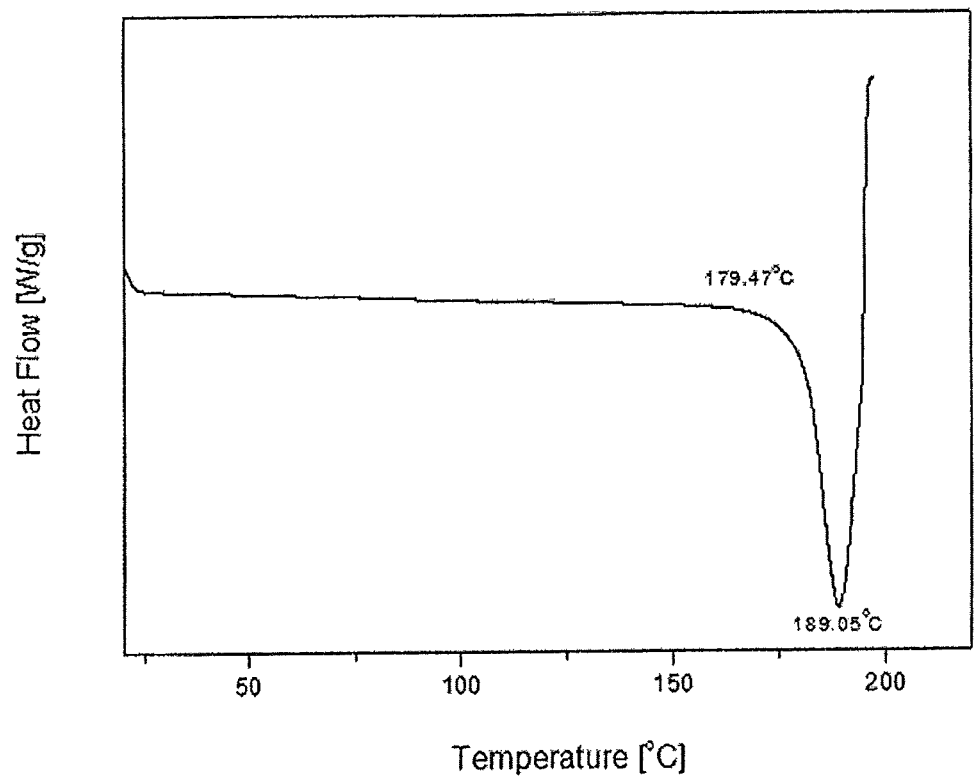
FIG. 13 shows a differential scanning calorimetry analysis result of the crystalline form II of 1-(5-(2,4-difluorophenyl)-1-((3-fluorophenyl)sulfonyl)-4-methoxy-1H-pyrrol-3-yl)-N-methylmethanamine fumarate prepared in Example 6-1.

Referring to FIG. 13, it could be confirmed that the crystalline form II of 1-(5-(2,4-difluorophenyl)-1-((3-fluorophenyl)sulfonyl)-4-methoxy-1H-pyrrol-3-yl)-N-methylmethanamine fumarate prepared in Example 6-1 had an endothermic initiation temperature of 179.47° C. and exhibited a maximum endothermic peak at an endothermic temperature of 189.05° C. in a differential scanning calorimetry analysis.

Figure 14:
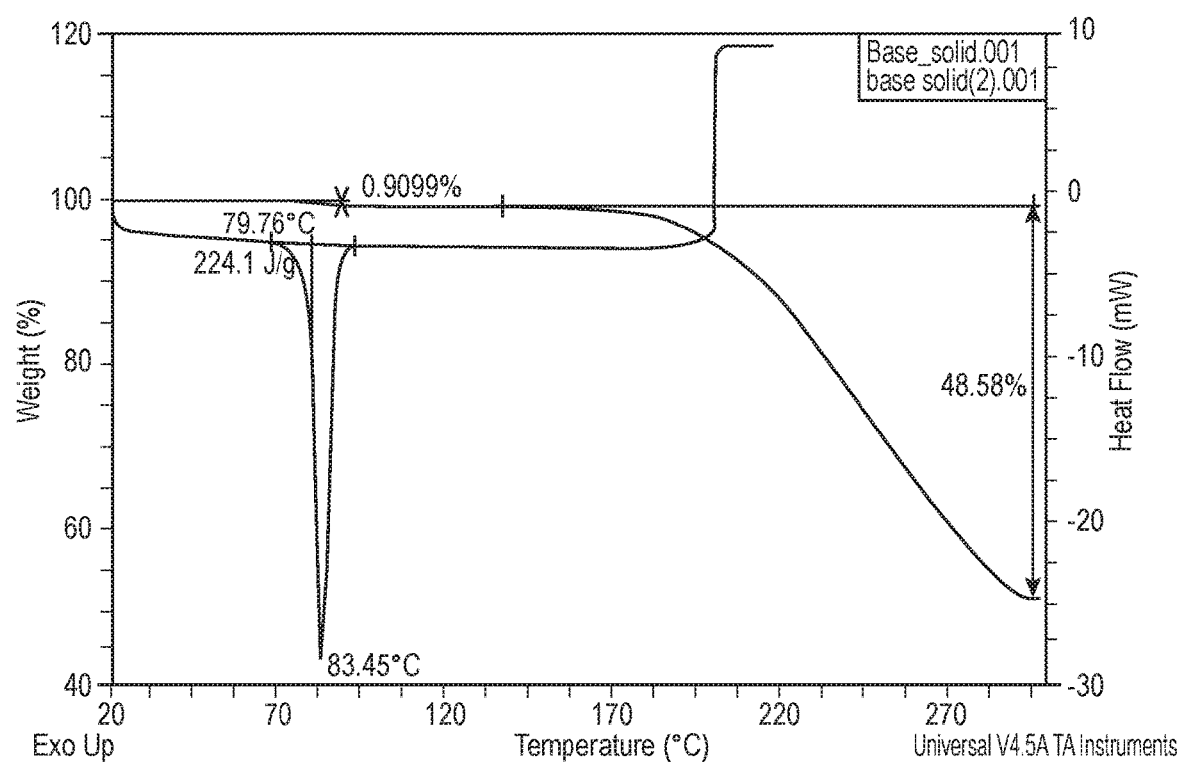
FIG. 14 shows a differential scanning calorimetry analysis result and thermogravimetric analysis result of the crystalline form of 1-(5-(2,4-difluorophenyl)-1-((3-fluorophenyl)sulfonyl)-4-methoxy-1H-pyrrol-3-yl)-N-methylmethanamine free base prepared in Comparative Example 1.

Referring to FIG. 14, it could be confirmed that the crystalline form of 1-(5-(2,4-difluorophenyl)-1-((3-fluorophenyl)sulfonyl)-4-methoxy-1H-pyrrol-3-yl)-N-methylmethanamine free base prepared in Comparative Example 1 had an endothermic initiation temperature of 79.76° C. and exhibited a maximum endothermic peak at an endothermic temperature of 83.45° C. in a differential scanning calorimetry analysis.

As can be seen from FIGS. 8 to 14, it could be confirmed that the crystalline form of 1-(5-(2,4-difluorophenyl)-1-((3-fluorophenyl)sulfonyl)-4-methoxy-1H-pyrrol-3-yl)-N-methylmethanamine free base prepared in Comparative Example 1 had a lower endothermic initiation temperature and a lower endothermic temperature with the maximum endothermic peak, compared to the crystalline forms of the salts prepared in Examples. Thus, it was confirmed that the crystalline form of 1-(5-(2,4-difluorophenyl)-1-((3-fluorophenyl)sulfonyl)-4-methoxy-1H-pyrrol-3-yl)-N-methylmethanamine free base was not suitable for the production of pharmaceuticals due to its low melting point, while the crystalline forms of the salts according to the Examples were pharmaceutically applicable.

Test Example 4: Hygroscopicity Test

The hygroscopicity test was carried out for the crystalline forms prepared in the above Examples. First, 40 mg of the crystalline forms of the Examples were tightly sealed and stored in each glass desiccator containing a saturated aqueous solution of several salts for at least two days under the condition of constant relative humidity as shown in Table 1 below. Subsequently, the result of measurement of weight change for each of these crystalline forms showed that weight change due to moisture was not observed. Accordingly, it could be seen that the crystalline forms prepared in the Examples did not have hygroscopicity.

TABLE 1

| Desiccator | Relative humidity | Types of salt-saturated aqueous solution |
|---|---|---|
| 1 | 33% | $MgCl_2$-saturated aqueous solution |
| 2 | 53% | $Mg(NO_3)_2 \cdot 6H_2O$-saturated aqueous solution |
| 3 | 64% | $NaNO_2$-saturated aqueous solution |
| 4 | 75% | NaCl-saturated aqueous solution |
| 5 | 93% | $KNO_3$-aqueous solution |

Test Example 5: Stability Confirmation Test

The stability test was carried out for the crystalline forms prepared in the Examples to evaluate the degree to which impurities were formed during storage under severe conditions (moisture-proof condition and high-humidity exposure condition). The results of the stability test under the moisture-proof condition were shown in Table 2 below, and the results of the stability test under the high-humidity exposure condition were shown in Table 3 below.

For the stability test, vials containing 10 mg of each sample which was precisely weighed and taken were prepared in the planned quantity, and they were stored by dividing into the moisture-proof condition (60° C. and less than 10% relative humidity) and under the high-humidity exposure condition (60° C. and 95% relative humidity). However, under the high-humidity exposure condition, a stopper of the vial was not used to keep so that the sample is in sufficient contact with a moisture in the air. At a fixed point of time after the initiation of the test, two vials per point of time were taken (number of samples per test n=2). 10 ml of methanol was added to each vial to dissolve the sample, which was then centrifuged. The resulting supernatant was analyzed using a liquid chromatography. The peak area was determined by integration for all detected peaks, and the relative peak area for the main component and the total impurity was calculated and expressed as an average value.

TABLE 2

| | | Initial | | After 2 weeks | | After 4 weeks | |
|---|---|---|---|---|---|---|---|
| | Types of crystalline form | Peak area of main component(%) | Peak area of total impurities (%) | Peak area of main component(%) | Peak area of total impurities (%) | Peak area of main component(%) | Peak area of total impurities(%) |
| Example 1-1 | Crystalline form I of hydrochloride | 99.82 | 0.18 | 99.80 | 0.19 | 99.80 | 0.20 |
| Example 3-1 | Crystalline form of succinate | 99.55 | 0.45 | 99.61 | 0.39 | 99.55 | 0.45 |
| Example 4-1 | Crystalline form of tartrate | 99.52 | 0.48 | 99.54 | 0.46 | 99.48 | 0.52 |
| Example 5-1 | Crystalline form II of fumarate | 99.38 | 0.62 | 99.36 | 0.64 | 99.37 | 0.63 |

TABLE 3

| | | Initial | | After 1 week | | After 2 weeks | | After 4 weeks | |
|---|---|---|---|---|---|---|---|---|---|
| | Type of crystalline form | Peak area of main component(%) | Peak area of total impurities (%) | Peak area of main component(%) | Peak area of total impurities (%) | Peak area of main component(%) | Peak area of total impurities (%) | Peak area of main component(%) | Peak area of total impurities (%) |
| Example 1-1 | Crystalline form I of hydrochloride | 99.82 | 0.18 | 99.81 | 0.19 | 99.80 | 0.20 | 99.80 | 0.20 |
| Example 3-1 | Crystalline form of succinate | 99.55 | 0.45 | 99.56 | 0.44 | 99.53 | 0.47 | 99.47 | 0.54 |
| Example 4-1 | Crystalline form of tartrate | 99.52 | 0.48 | 99.48 | 0.52 | 99.43 | 0.57 | 99.23 | 0.77 |
| Example 5-1 | Crystalline form I of fumarate | 99.38 | 0.62 | 99.40 | 0.60 | 99.32 | 0.68 | 99.30 | 0.70 |

As shown in Tables 2 and 3, it could be confirmed that the crystalline forms prepared in the Examples did not show a decrease in the peak area of the main component and an increase in the peak area of the total impurities which were significant under the moisture-proof condition and the high-humidity exposure condition. Therefore, it was confirmed that the crystalline forms produced in the Examples suppressed an increase of impurities regardless of the influence of humidity under severe conditions and exhibited excellent chemical stability.

Test Example 6: Solubility Test in Water

The solubility test in water was carried out for the crystal form prepared in the Examples, and the results were shown in Table 4 below. For the solubility test in water, a sample of less than 10 mg was first precisely weighed and taken and placed into a vial, to which 50 μl of deionized water was added, shaking for 30 seconds and ultrasonic shaking for 1 minute were carried out, and these processes were repeated several times. The water solubility was calculated by measuring the amount of water used to dissolve all the samples.

TABLE 4

| | Type of crystalline form | Solubility in water (mg/ml) |
| --- | --- | --- |
| Example 1-1 | Crystalline form I of hydrochloride | 11.11 |
| Example 3-1 | Crystalline form of succinate | 7.20 |
| Example 4-1 | Crystalline form of tartrate | 6.90 |
| Example 5-1 | Crystalline form I of fumarate | 1.73-2.60 |
| Comparative Example 1 | Crystalline form of free base | Less than 0.16 |

As shown in Table 4, it could be seen that the crystalline forms prepared in the Examples had a water solubility of 10 times or more as compared with that of the crystalline form of the free base prepared in Comparative Example 1. In addition, the crystalline forms prepared in the Examples showed high solubility in the order of crystalline form I of hydrochloride, crystalline form of succinate, crystalline form of tartrate and crystalline form I of fumarate.

What is claimed is:

1. A crystalline form of 1-(5-(2,4-difluorophenyl)-1-((3-fluorophenyl)sulfonyl)-4-methoxy-1H-pyrrol-3-yl)-N-methylmethanamine tartrate having peaks at diffraction angles (2θ±0.2°) of 11.7°, 21.5° and 23.5° in an X-ray powder diffraction pattern.

2. The crystalline form of 1-(5-(2,4-difluorophenyl)-1-((3-fluorophenyl)sulfonyl)-4-methoxy-1H-pyrrol-3-yl)-N-methylmethanamine tartrate of claim 1, wherein the crystalline form has an endothermic initiation temperature of 146.34±3° C. and exhibits a maximum endothermic peak at an endothermic temperature of 148.27±3° C. in a differential scanning calorimetry analysis.

* * * * *